(12) United States Patent
Allin et al.

(10) Patent No.: US 10,130,518 B2
(45) Date of Patent: Nov. 20, 2018

(54) APPURTENANCES INCLUDING SENSORS FOR REPORTING INFORMATION REGARDING WOUND DRESSINGS

(71) Applicant: Elwha LLC, Bellevue, WA (US)

(72) Inventors: Boyd D. Allin, Seattle, WA (US); Jared Drinkwater, Auburn, WA (US); Paul Duesterhoft, Issaquah, WA (US); Nicholas Dykstra, Seattle, WA (US); Daniel Hawkins, Pleasanton, CA (US); Roderick A. Hyde, Redmond, WA (US); Jordin T. Kare, Seattle, WA (US); Eric C. Leuthardt, St. Louis, MO (US); Levi M. Miller, Seattle, WA (US); Elizabeth L. Schubert, Bellevue, WA (US); Clarence T. Tegreene, Mercer Island, WA (US); Lowell L. Wood, Jr., Bellevue, WA (US)

(73) Assignee: ELWHA LLC, Bellevue, WA (US)

( * ) Notice: Subject to any disclaimer, the term of this patent is extended or adjusted under 35 U.S.C. 154(b) by 712 days.

(21) Appl. No.: 14/252,049

(22) Filed: Apr. 14, 2014

(65) Prior Publication Data

US 2014/0298927 A1    Oct. 9, 2014

Related U.S. Application Data

(63) Continuation-in-part of application No. 13/445,174, filed on Apr. 12, 2012, which is a continuation-in-part
(Continued)

(51) Int. Cl.
*A61F 13/00* (2006.01)
*A61B 5/00* (2006.01)
(Continued)

(52) U.S. Cl.
CPC ........ *A61F 13/00051* (2013.01); *A61B 5/002* (2013.01); *A61B 5/0022* (2013.01);
(Continued)

(58) Field of Classification Search
CPC .................................................. A61M 1/0088
(Continued)

(56) References Cited

U.S. PATENT DOCUMENTS 3,927,669 A * 12/1975 Glatt ................. A61F 13/00021
                                                602/47
4,384,288 A    5/1983 Walton
(Continued)

FOREIGN PATENT DOCUMENTS

EP      0 430 608 A1    6/1991
WO      WO 00/08203     2/2000
(Continued)

OTHER PUBLICATIONS

U.S. Appl. No. 14/719,639, Duesterhoft et al.
(Continued)

*Primary Examiner* — May Abouelela
(74) *Attorney, Agent, or Firm* — Dorsey & Whitney LLP

(57) ABSTRACT

In some embodiments, an appurtenance to a wound dressing includes: a substrate with at least one surface of a size and shape to mate with a surface of a wound dressing; a plurality of projections attached to the substrate and positioned to secure the substrate to the wound dressing; one or more sensor units attached to the substrate, the one or more sensor units configured to sense a condition of the wound dressing; and a transmission unit attached to the substrate and operably coupled to the one or more sensor units, the transmission unit including circuitry configured to transmit information associated with the one or more sensor units.

18 Claims, 15 Drawing Sheets

Related U.S. Application Data of application No. 13/445,220, filed on Apr. 12, 2012, now Pat. No. 9,084,530.

(51) Int. Cl.
*G06F 19/00* (2018.01)
*G16H 40/67* (2018.01)
*A61M 1/00* (2006.01)
*A61B 5/145* (2006.01)

(52) U.S. Cl.
CPC .......... *A61B 5/445* (2013.01); *A61M 1/0025* (2014.02); *G06F 19/00* (2013.01); *G16H 40/67* (2018.01); *A61B 5/14539* (2013.01); *A61M 1/0088* (2013.01); *A61M 2205/3344* (2013.01); *A61M 2205/3382* (2013.01); *A61M 2205/3553* (2013.01); *A61M 2205/3592* (2013.01); *A61M 2230/50* (2013.01)

(58) Field of Classification Search
USPC ............ 600/573, 586, 583; 604/319; 602/42
See application file for complete search history.

(56) References Cited

U.S. PATENT DOCUMENTS

| | | | | |
|---|---|---|---|---|
| 4,430,998 A | * | 2/1984 | Harvey | A61B 17/085 606/216 |
| 4,753,232 A | * | 6/1988 | Ward | A61F 13/023 602/52 |
| 4,924,866 A | | 5/1990 | Yoon | |
| 5,047,047 A | * | 9/1991 | Yoon | A61B 17/083 606/213 |
| 5,507,775 A | * | 4/1996 | Ger | A61B 17/08 606/215 |
| 5,704,352 A | | 1/1998 | Tremblay et al. | |
| 5,876,365 A | | 3/1999 | Hart | |
| 5,904,671 A | * | 5/1999 | Navot | A61F 13/20 340/573.5 |
| 5,912,114 A | | 6/1999 | Hutchinson et al. | |
| 5,939,205 A | | 8/1999 | Yokoyama et al. | |
| 5,964,723 A | * | 10/1999 | Augustine | A61F 7/007 602/2 |
| 5,986,163 A | | 11/1999 | Augustine | |
| 6,037,879 A | | 3/2000 | Tuttle | |
| 6,248,084 B1 | | 6/2001 | Augustine et al. | |
| 6,270,455 B1 | | 8/2001 | Brown | |
| 6,283,938 B1 | | 9/2001 | McConnell | |
| 6,348,640 B1 | | 2/2002 | Navot et al. | |
| 6,420,622 B1 | | 7/2002 | Johnston et al. | |
| 6,569,189 B1 | * | 5/2003 | Augustine | A61F 7/007 602/14 |
| 6,693,513 B2 | * | 2/2004 | Tuttle | G06K 19/0716 340/10.1 |
| 6,863,220 B2 | | 3/2005 | Selker | |
| 6,889,165 B2 | | 5/2005 | Lind et al. | |
| 6,963,772 B2 | | 11/2005 | Bloom et al. | |
| 7,030,764 B2 | | 4/2006 | Smith et al. | |
| 7,055,754 B2 | | 6/2006 | Forster | |
| 7,215,976 B2 | | 5/2007 | Brideglall | |
| 7,297,112 B2 | | 11/2007 | Zhou et al. | |
| 7,361,184 B2 | | 4/2008 | Joshi | |
| 7,372,780 B1 | | 5/2008 | Braunberger | |
| 7,411,505 B2 | | 8/2008 | Smith et al. | |
| 7,446,660 B2 | | 11/2008 | Posamentier | |
| 7,479,886 B2 | | 1/2009 | Burr | |
| 7,507,675 B2 | | 3/2009 | Zuilhof et al. | |
| 7,520,872 B2 | * | 4/2009 | Biggie | A61M 1/0088 601/6 |
| 7,612,424 B1 | | 11/2009 | Espinosa et al. | |
| 7,666,151 B2 | | 2/2010 | Sullivan et al. | |
| 7,667,606 B2 | | 2/2010 | Packert et al. | |
| 7,703,334 B2 | | 4/2010 | Cochran | |
| 7,724,136 B2 | | 5/2010 | Posamentier | |
| 7,794,925 B2 | | 9/2010 | Cullen | |
| 7,813,226 B2 | | 10/2010 | Braunberger | |
| 7,825,776 B2 | | 11/2010 | Smith et al. | |
| 7,838,717 B2 | * | 11/2010 | Haggstrom | A61F 13/0203 128/888 |
| 7,883,494 B2 | | 2/2011 | Martin | |
| 7,896,856 B2 | | 3/2011 | Petrosenko et al. | |
| 7,914,867 B2 | | 3/2011 | Mori et al. | |
| 7,945,302 B2 | | 5/2011 | McAdams | |
| 7,951,605 B2 | | 5/2011 | Pitner et al. | |
| 7,964,390 B2 | | 6/2011 | Rozakis et al. | |
| 7,986,235 B2 | | 7/2011 | Posamentier | |
| 8,014,234 B2 | | 9/2011 | Braunberger | |
| 8,048,046 B2 | * | 11/2011 | Hudspeth | A61M 1/0088 604/119 |
| 8,057,446 B2 | * | 11/2011 | Kane | A61F 13/0203 604/304 |
| 8,257,328 B2 | * | 9/2012 | Augustine | A61M 1/0049 604/313 |
| 8,350,116 B2 | | 1/2013 | Lockwood et al. | |
| 8,376,972 B2 | * | 2/2013 | Fleischmann | A61F 13/00068 601/6 |
| 8,690,845 B2 | | 4/2014 | Long et al. | |
| 8,760,295 B2 | * | 6/2014 | Forster | A61B 5/445 340/425.2 |
| 8,785,713 B2 | * | 7/2014 | Hong | A61L 15/425 602/41 |
| 8,795,257 B2 | * | 8/2014 | Coulthard | A61M 1/0031 604/313 |
| 8,808,274 B2 | | 8/2014 | Hartwell | |
| 8,945,030 B2 | * | 2/2015 | Weston | A61M 1/0088 602/2 |
| 8,946,499 B2 | * | 2/2015 | Iyer | A61L 15/42 602/41 |
| 9,011,393 B2 | | 4/2015 | Kazala, Jr. et al. | |
| 9,050,398 B2 | | 6/2015 | Armstrong et al. | |
| 9,168,180 B2 | * | 10/2015 | Ha | A61F 13/02 |
| 9,422,934 B2 | * | 8/2016 | Locke | F04B 53/00 |
| 2003/0199783 A1 | | 10/2003 | Bloom et al. | |
| 2003/0216663 A1 | | 11/2003 | Jersey-Willuhn et al. | |
| 2004/0073151 A1 | | 4/2004 | Weston | |
| 2004/0210280 A1 | | 10/2004 | Liedtke | |
| 2006/0036145 A1 | | 2/2006 | Brister et al. | |
| 2006/0047218 A1 | | 3/2006 | Bloom et al. | |
| 2007/0171076 A1 | | 7/2007 | Stevens et al. | |
| 2007/0203442 A1 | | 8/2007 | Bechert et al. | |
| 2007/0204691 A1 | | 9/2007 | Bogner et al. | |
| 2007/0231380 A1 | | 10/2007 | Shah et al. | |
| 2007/0247316 A1 | | 10/2007 | Wildman et al. | |
| 2007/0252712 A1 | | 11/2007 | Allen et al. | |
| 2007/0269851 A1 | | 11/2007 | Sanders et al. | |
| 2008/0132821 A1 | | 6/2008 | Propp et al. | |
| 2008/0166397 A1 | | 7/2008 | Trotter et al. | |
| 2008/0171957 A1 | | 7/2008 | Connolly et al. | |
| 2008/0234616 A1 | * | 9/2008 | Shives | A61F 13/00068 602/13 |
| 2009/0167495 A1 | | 7/2009 | Smith et al. | |
| 2009/0192369 A1 | | 7/2009 | Say et al. | |
| 2009/0209883 A1 | | 8/2009 | Higgins et al. | |
| 2009/0227969 A1 | | 9/2009 | Jaeb et al. | |
| 2009/0243813 A1 | | 10/2009 | Smith et al. | |
| 2009/0299161 A1 | | 12/2009 | Cullen et al. | |
| 2010/0010477 A1 | | 1/2010 | Augustine et al. | |
| 2010/0022990 A1 | | 1/2010 | Karpowicz et al. | |
| 2010/0030167 A1 | | 2/2010 | Thirstrup et al. | |
| 2010/0100061 A1 | | 4/2010 | Odland | |
| 2010/0125258 A1 | | 5/2010 | Coulthard et al. | |
| 2010/0166694 A1 | | 7/2010 | Stephens et al. | |
| 2010/0204606 A1 | | 8/2010 | Kim et al. | |
| 2010/0228206 A1 | * | 9/2010 | Larsson | A61M 1/0084 604/319 |
| 2010/0249733 A9 | | 9/2010 | Slott et al. | |
| 2010/0318052 A1 | * | 12/2010 | Ha | A61F 13/02 604/385.01 |
| 2010/0331634 A1 | | 12/2010 | Müller et al. | |
| 2011/0015591 A1 | | 1/2011 | Hanson et al. | |
| 2011/0034906 A1 | | 2/2011 | Malhi | |
| 2011/0054340 A1 | | 3/2011 | Russ et al. | |

(56) References Cited

U.S. PATENT DOCUMENTS

| | | |
|---|---|---|
| 2011/0082356 A1 | 4/2011 | Yang et al. |
| 2011/0092927 A1* | 4/2011 | Wilkes .............. A61F 13/00059 604/304 |
| 2011/0105854 A1 | 5/2011 | Kiani et al. |
| 2011/0140703 A1 | 6/2011 | Chiao et al. |
| 2011/0160548 A1 | 6/2011 | Forster |
| 2011/0172582 A1* | 7/2011 | Darian .................. A61F 15/004 602/79 |
| 2011/0178375 A1 | 7/2011 | Forster |
| 2011/0213559 A1 | 9/2011 | Pollack et al. |
| 2012/0010099 A1 | 1/2012 | Stephens et al. |
| 2012/0016322 A1 | 1/2012 | Coulthard et al. |
| 2012/0035560 A1 | 2/2012 | Eddy et al. |
| 2012/0078157 A1* | 3/2012 | Ravikumar ............... A61F 5/34 602/79 |
| 2012/0109034 A1* | 5/2012 | Locke ..................... A61F 13/02 602/42 |
| 2012/0130325 A1 | 5/2012 | Blott et al. |
| 2012/0238931 A1 | 9/2012 | Rastegar et al. |
| 2012/0245540 A1 | 9/2012 | Zimnitsky et al. |
| 2013/0053799 A1 | 2/2013 | Locke et al. |
| 2013/0261409 A1 | 10/2013 | Pathak et al. |
| 2013/0304006 A1 | 11/2013 | Toth |
| 2013/0304007 A1* | 11/2013 | Toth .................... A61M 1/0031 604/321 |
| 2013/0317405 A1* | 11/2013 | Ha ..................... A61F 13/0226 602/42 |
| 2013/0317406 A1 | 11/2013 | Locke et al. |
| 2015/0208961 A1 | 7/2015 | Duesterhoft et al. |
| 2015/0290045 A1 | 10/2015 | Fan et al. |

FOREIGN PATENT DOCUMENTS

| | | | |
|---|---|---|---|
| WO | WO 03/040406 A2 | 5/2003 | |
| WO | WO 2005/009328 A1 | 2/2005 | |
| WO | WO 2007/130239 A1 | 11/2007 | |
| WO | WO 2012/057882 A1 | 5/2012 | |

OTHER PUBLICATIONS

U.S. Appl. No. 14/252,136, Duesterhoft et al.
U.S. Appl. No. 13/795,667, Duesterhoft et al.
U.S. Appl. No. 13/491,677, Duesterhoft et al.
U.S. Appl. No. 13/445,220, Duesterhoft et al.
U.S. Appl. No. 13/445,174, Duesterhoft et al.
Abhisam; "RFID systems for pharmaceutical distributors to meet the new FDA regulations on drugs"; Discover the power of e-learning!; bearing a date of 2006; pp. 1-7; Abhisam Software.
Alien Technology; "Battery Assisted Passive Tags"; Alien Technology brochure; downloaded from the web Oct. 17, 2011; pp. 1-2; located at: http://www.alientechnology.com/docs/AT_DS_BAP.pdf; Alien Technology Corp.
Berggren et al.; "Capacitive Biosensors"; Electroanalysis; bearing a date of 2001; pp. 173-180; vol. 13, No. 3; WILEY-VCH Verlag GmbH.
Bluestein et al.; "Pressure Ulcers: Prevention, Evaluation, and Management"; American Family Physician; Nov. 15, 2008; pp. 1186-1194; vol. 78, No. 10; American Academy of Family Physicians.
"Body-fluid battery"; Science News; Sep. 10, 2005; pp. 1-2; located at http://findarticles.com/p/articles/mi_ml200/is_11_168/ai_n15674798/; Science Service, Inc. and Gale Group.
Chawla et al.; "An Overview of Passive RFID"; IEEE Applications & Practice; Sep. 2007; pp. 11-17; IEEE.
Chen et al.; "A 2G-RFID-Based E-Healthcare System"; IEEE Wireless Communications; Feb. 2010; pp. 37-43; IEEE.
Chen et al.; "Ultrasonic Measurement System with Infrared Communication Technology"; Journal of Computers; Nov. 2011; pp. 2468-2475; vol. 6, No. 11; Academy Publisher.

Clay, Karen S.; "Preventing pressure ulcers in your facility: Karen S. Clay, RN, BSN, CWCN, presents a primer on how to protect frail residents—and avoid costly reprimands"; 2004; 14 pages; HCPro, Inc.
Collier, Mark; "Recognition and management of wound infections"; World Wide Wounds; Jan. 2004; pp. 1-9.
Cui et al.; "Nanowire Nanosensors for Highly Sensitive and Selective Detection of Biological and Chemical Species"; Science; Aug. 17, 2001; pp. 1289-1292, and 1 cover page; vol. 293; American Association for the Advancement of Science.
Cutting et al.; "Criteria for identifying wound infection"; Journal of Wound Care; Jun. 1994; pp. 198-201; vol. 3, No. 4.
Dehennis et al.; "A Wireless Microsystem for the Remote Sensing of Pressure, Temperature, and Relative Humidity"; Journal of Microelectromechanical Systems; Feb. 2005; pp. 12-22; vol. 14, No. 1; IEEE.
Dowd et al.; "Survey of bacterial diversity in chronic wounds using Pyrosequencing, DGGE, and full ribosome shotgun sequencing"; BMC Microbiology; 2008; pp. 1-15; vol. 8, No. 43; BioMed Central Ltd.
Fadlullah et al; "Indoor High-Bandwidth Optical Wireless Links for Sensor Networks"; Journal of Lightwave Technology; Nov. 1, 2010; pp. 3086-3094; vol. 28, No. 21; IEEE.
Finkenzeller, Klaus; "Fundamental Operating Principles" Chapter 3 of the RFID Handbook: Fundamentals and Applications in Contactless Smart Cards and Identification; bearing a date of 2003; pp. 29-59; John Wiley & Sons, Ltd.
Fisher et al.; "Tracking the social dimensions of RFID systems in hospitals"; International Journal of Medical Informatics; bearing a date of 2008; pp. 176-183; vol. 77; Elsevier Ireland Ltd.
Fisher, Jill A.; "Indoor Positioning and Digital Management: Emerging Surveillance Regimes in Hospitals"; Chapter 5 in T. Monahan (Ed), Surveillance and Security: Technological Politics and Power in Everyday Life; May 23, 2006; pp. 77-88; Routledge.
Frost & Sullivan; "Advances in Wound Healing Techniques"; Technical Insights; Publication D11A; bearing a date of 2008; pp. 1-118; Frost & Sullivan.
Frost & Sullivan; "An Overview of Ulceration Wounds"; Publication M4BB-54; Dec. 2009; pp. 1-77; Frost & Sullivan.
Frost & Sullivan; "U.S. Advanced Wound Care Market"; Publication N71A-54; Aug. 2010; pp. 1-90; Frost & Sullivan.
Goodisman, Jerry; "Observations on Lemon Cells"; Journal of Chemical Education; Apr. 2001; pp. 516-518; vol. 78, No. 4.
Gray, David; "Assessment, Diagnosis and Treatment of Infection"; Wounds UK; bearing a date of 2011; pp. 4-9; vol. 7, No. 2, supplement.
Grist et al.; "Optical Oxygen Sensors for Applications in Microfluidic Cell Culture"; Sensors; 2010; pp. 9286-9316; vol. 10; MDPI; Basel, Switzerland.
Huang et al.; "Development of an $IrO_x$ Micro pH Sensor Array on Flexible Polymer Substrate"; Nanosensors and Microsensors for Bio-Systems 2008, edited by Vijay K. Varadan, Proc. of SPIE, vol. 6931, 693104; 2008; pp. 1-9.
Huang et al.; "Investigation of Repeatability of Sol-Gel Iridium Oxide pH Sensor on Flexible Substrate"; Micro- and Nanotechnology: Materials, Processes, Packaging, and Systems IV, edited by Jung-Chih Chiao et al., Proc. of SPIE, vol. 7269, 726916; 2008; pp. 1-9.
Ibridge Network; "pH Sensor Array on Flexible Substrate for Wound Care (UTA Ref. No. 08-21)"; Nov. 28, 2011; pp. 1-2; Kauffman Innovation Network, Inc.
Intel; "WISP: Wireless Identification and Sensing Platform"; Intel Labs Seattle; printed on Oct. 8, 2011; pp. 1-4; located at http://www.seattle.intel-research.net/WISP/.
Intelleflex; "Worldwide RFID UHF Map"; printed on Oct. 17, 2011; p. 1; located at: http://www.intelleflex.com/pdf/Worldwide_UHF_Chart.pdf ; Intelleflex Corporation.
Karthik MNS; "Could blood be used to power batteries?"; Feb. 2009; pp. 1-4; located at: http://hoowstuffworks.blogspot.com/2009/02/could-blood-be-used-to-power-batteries.html.
Kavehrad, Mohsen; "Sustainable Energy-Efficient Wireless Applications Using Light"; IEEE Communications Magazine; Dec. 2010; pp. 66-73; IEEE.

(56) References Cited

OTHER PUBLICATIONS

Kelly-Quintos et al.; "Characterization of the Opsonic and Protective Activity Against *Staphylococcus aureus* of Fully Human Monoclonal Antibodies Specific for the Bacterial Surface Polysaccharide Poly-N-Acetylglucosamine"; Infection and Immunity; May 2006; pp. 2742-2750; vol. 74, No. 5; American Society for Microbiology.
Lee et al.; "Water Activated Disposable and Long Shelf Life Microbatteries"; 2003; pp. 387-390; IEEE.
Lim et al.; "A Micromechanical Biosensor with Interdigitated Capacitor Readout"; Proceedings of the 2011 IEEE/ICME International Conference on Complex Medical Engineering; May 22-25, 2011; pp. 42-46; IEEE.
Löfgren et al.; "Low-power humidity sensor for RFID applications"; Multi-Material Micro Manufacture; 2008; 4 pages; Cardiff University.
McColl et al.; "Monitoring moisture without disturbing the wound dressing"; Wounds UK; bearing a date of 2009; pp. 94-96, and 98-99; vol. 5, No. 3.
Mehmood et al.; "Applications of modern sensors and wireless technology in effective wound management"; Journal of Biomedical Materials Research B: Applied Biomaterials; 2013; pp. 1-11; Wiley Peridicals Inc.
Murata Manufacturing Co., Ltd.; "Piezoelectric Sound Components"; Cat. No. P37E-23; Nov. 2009; pp. 1-33, and two cover pages.
Murata Manufacturing Co., Ltd.; "Ultrasonic Sensor Application Manual"; Cat. No. S15E-5; Aug. 2009; pp. 1-3, and 2-14, and one supplemental page.
Nature News; "A miniature biofuel cell operating in a physiological buffer"; Nature; Nov. 12, 2002; pp. 1-2; located at http://www.nature.com/news/2002/021112/full/news021111-1.html.
Ohno et al.; "Graphene Field-Effect Transistors for Label-Free Biological Sensors"; IEEE Sensors 2010 Conference Proceedings; Nov. 1-4, 2010; pp. 903-906; IEEE.
Pacific Northwest National Laboratory; "Juvenile Salmon Acoustic Telemetry System (JSATS) Acoustic Transmitters"; Mar. 2010; pp. 1-2.
Pan et al.; "Development of the real-time pH sensing system for array sensors"; Sensors and Actuators B 108; 2005; pp. 870-876; Elsevier B.V.
Patauner et al.; "High Speed RFID/NFC at the Frequency of 13.56 MHz"; presented at the First International EURASIP Workshop on RFID Technology; Sep. 24-25, 2007; pp. 1-4.
PCT International Search Report; International App. No. PCT/US2013/035993; dated Jun. 25, 2013; pp. 1-2.
PCT International Search Report; International App. No. PCT/US13/36000; dated Jul. 5, 2013; pp. 1-3.
Pushparaj et al.; "Flexible energy storage devices based on nanocomposite paper"; PNAS; Aug. 21, 2007; pp. 13574-13577; vol. 104, No. 34; The National Academy of Sciences of the USA.
Ruhanen et al.; "Sensor-enabled RFID tag handbook"; Building Radio Frequency Identification for the Global Environment; Jan. 2008; pp. 1-47; IST-2005-033546; European Commission.
Sammoura et al.; "Water-activated disposable and long shelf life microbatteries"; Sensors and Actuators A 111; 2004; pp. 79-86; Elsevier B.V.
Sample et al.; "A Capacitive Touch Interface for Passive RFID Tags"; IEEE International Conference on RFID; Apr. 27-28, 2009; pp. 103-109; IEEE.
Sample et al.; "Design of an RFID-Based Battery-Free Programmable Sensing Platform"; IEEE Transactions on Instrumentation and Measurement; Nov. 2008; pp. 2608-2615; vol. 57, No. 11; IEEE.
Sample et al.; "Photovoltaic Enhanced UHF RFID Tag Antennas for Dual Purpose Energy Harvesting"; 2011 International Conference on RFID; Apr. 12-14, 2011; pp. 146-153; IEEE.
Sidén et al.; "The 'Smart' Diaper Moisture Detection System"; IEEE MTT-S Digest, WE4B-3; 2004; pp. 659-662; IEEE.
Stevens et al.; "RuBee (IEEE 1902.1)—The Physics Behind, Real-Time, High Security Wireless Asset Visibility Networks in Harsh Environments"; Sep. 2010; retrieved from web Nov. 17, 2011; pp. 1-6; located at: http://www.rubee.com/White-SEC/RuBee-Security-080610.pdf.
Tehrani et al.; "Detection of Monoclonal Antibodies using Chemically Modified Graphite Substrates"; IEEE Sensors 2010 Conference Proceedings; Nov. 1-4, 2010; pp. 428-431; IEEE.
University of Texas Arlington, Office of Technology Management; "Smart Wound Condition Monitoring pH Sensor Array on Flexible Substrate"; Technology Summary; printed on Apr. 12, 2012; pp. 1-2.
Visible Assets; "RuBee Technology, Real-Time Asset Visibility"; printed from web Nov. 17, 2011; pp. 1-3; located at: http://www.rubee.com/Techno/index.html ;Visible Assets.
Wang, Wencheng; "A Design Method of Ultrasonic Ranging System with High Accuracy"; Journal of Computational Information Systems; Jul. 2011; pp. 2444-2451; vol. 7, No. 7; Binary Information Press.
Yeager et al.; "Wirelessly-Charged UHF Tags for Sensor Data Collection"; 2008 IEEE International Conference on RFID; Apr. 16-17, 2008; pp. 320-327; IEEE.
European Search Report; European App. No. EP 13 77 5331; dated Nov. 6, 2015 (received by our Agent on Nov. 12, 2015); pp. 1-3.
European Search Report; European App. No. EP 13 77 5973; dated Nov. 4, 2015 (received by our Agent on Nov. 12, 2015); pp. 1-3.
European Patent Office; Communication pursuant to Article 94(3) EPC; App. No. EP 13 775 331.5; dated Feb. 15, 2017 (received by our Agent on Feb. 15, 2017); pp. 1-4.
European Patent Office; Communication pursuant to Article 94(3) EPC; App. No. EP 13 775 973.4; dated Feb. 14, 2017 (received by our Agent on Feb. 14, 2017); pp. 1-4.

\* cited by examiner

APPURTENANCES INCLUDING SENSORS FOR REPORTING INFORMATION REGARDING WOUND DRESSINGS

If an Application Data Sheet (ADS) has been filed on the filing date of this application, it is incorporated by reference herein. Any applications claimed on the ADS for priority under 35 U.S.C. §§ 119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application claims the benefit of the earliest available effective filing date(s) from the following listed application(s) (the "Priority Applications"), if any, listed below (e.g., claims earliest available priority dates for other than provisional patent applications or claims benefits under 35 USC § 119(e) for provisional patent applications, for any and all parent, grandparent, great-grandparent, etc. applications of the Priority Application(s)).

PRIORITY APPLICATIONS

The present application constitutes a continuation-in-part of U.S. patent application Ser. No. 13/445,174, entitled APPURTENANCES FOR REPORTING INFORMATION REGARDING WOUND DRESSINGS, naming Paul Duesterhoft, Nicholas Dykstra, Daniel Hawkins, Roderick A. Hyde, Jordin T. Kare, Eric C. Leuthardt, Elizabeth L. Schubert, Clarence T. Tegreene, and Lowell L. Wood, Jr. as inventors, filed 12 Apr. 2012, which is currently co-pending or is an application of which a currently co-pending application is entitled to the benefit of the filing date, and which is a continuation-in-part of U.S. patent application Ser. No. 13/445,220, entitled COMPUTATIONAL METHODS AND SYSTEMS FOR REPORTING INFORMATION REGARDING APPURTENANCES TO WOUND DRESSINGS, naming Paul Duesterhoft, Nicholas Dykstra, Daniel Hawkins, Roderick A. Hyde, Jordin T. Kare, Eric C. Leuthardt, Elizabeth L. Schubert, Clarence T. Tegreene, and Lowell L. Wood, Jr. as inventors, filed 12 Apr. 2012.

If the listings of applications provided above are inconsistent with the listings provided via an ADS, it is the intent of the Applicant to claim priority to each application that appears in the Domestic Benefit/National Stage Information section of the ADS and to each application that appears in the Priority Applications section of this application.

All subject matter of the Priority Applications and of any and all applications related to the Priority Applications by priority claims (directly or indirectly), including any priority claims made and subject matter incorporated by reference therein as of the filing date of the instant application, is incorporated herein by reference to the extent such subject matter is not inconsistent herewith.

SUMMARY

In some embodiments, an appurtenance to a wound dressing includes: a substrate with at least one surface of a size and shape to mate with a surface of a wound dressing; a plurality of projections attached to the substrate and positioned to secure the substrate to the wound dressing; one or more sensor units attached to the substrate, the one or more sensor units configured to sense a condition of the wound dressing; and a transmission unit attached to the substrate and operably coupled to the one or more sensor units, the transmission unit including circuitry configured to transmit information associated with the one or more sensor units. In some embodiments, an appurtenance to a wound dressing includes: an enclosure including at least one external surface of a size and shape to mate with a surface of a wound dressing; one or more sensor units affixed to the enclosure, the one or more sensor units configured to sense a condition of the wound dressing; a processor operably coupled to the one or more sensor units; and at least one transmission unit operably coupled to the processor, the transmission unit including circuitry configured to transmit information associated with the one or more sensor units. In some embodiments, an appurtenance to a wound dressing includes: an enclosure including an external surface, the external surface including a first portion of a size and shape to mate with an aperture in a wound dressing, the external surface including a second portion including a surface facing away from an exterior of the wound dressing; a flange attached to the external surface of the enclosure on or proximal to the second portion, the flange including a surface configured to mate with an outward-facing surface of the wound dressing; an end cap attached to the external surface of the enclosure; one or more sensor units affixed to the enclosure, the one or more sensor units including circuitry configured to sense a condition of a wound dressing environment; a processor operably coupled to the one or more sensor units; and at least one transmission unit operably coupled to the processor and operably coupled to the one or more sensor units, the transmission unit including circuitry configured to transmit information associated with the one or more sensor units. In some embodiments, an appurtenance to a wound dressing includes: a substrate with a surface of a size and shape to mate with a surface of a wound dressing; a resonance sensor unit secured to the substrate; and an attachment unit of a size and shape to affix the substrate to the wound dressing with the surface in direct contact with the surface of the wound dressing.

In some embodiments, a wound dressing monitoring system includes: a wound dressing including at least one aperture; and an appurtenance, including an enclosure including at least one external surface of a size and shape to mate with an internal surface of the aperture in the wound dressing, one or more sensor units secured to the enclosure, a processor operably attached to the one or more sensor units, and at least one transmission unit operably attached to the processor, the transmission unit including circuitry configured to transmit information associated with the one or more sensor units.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1:
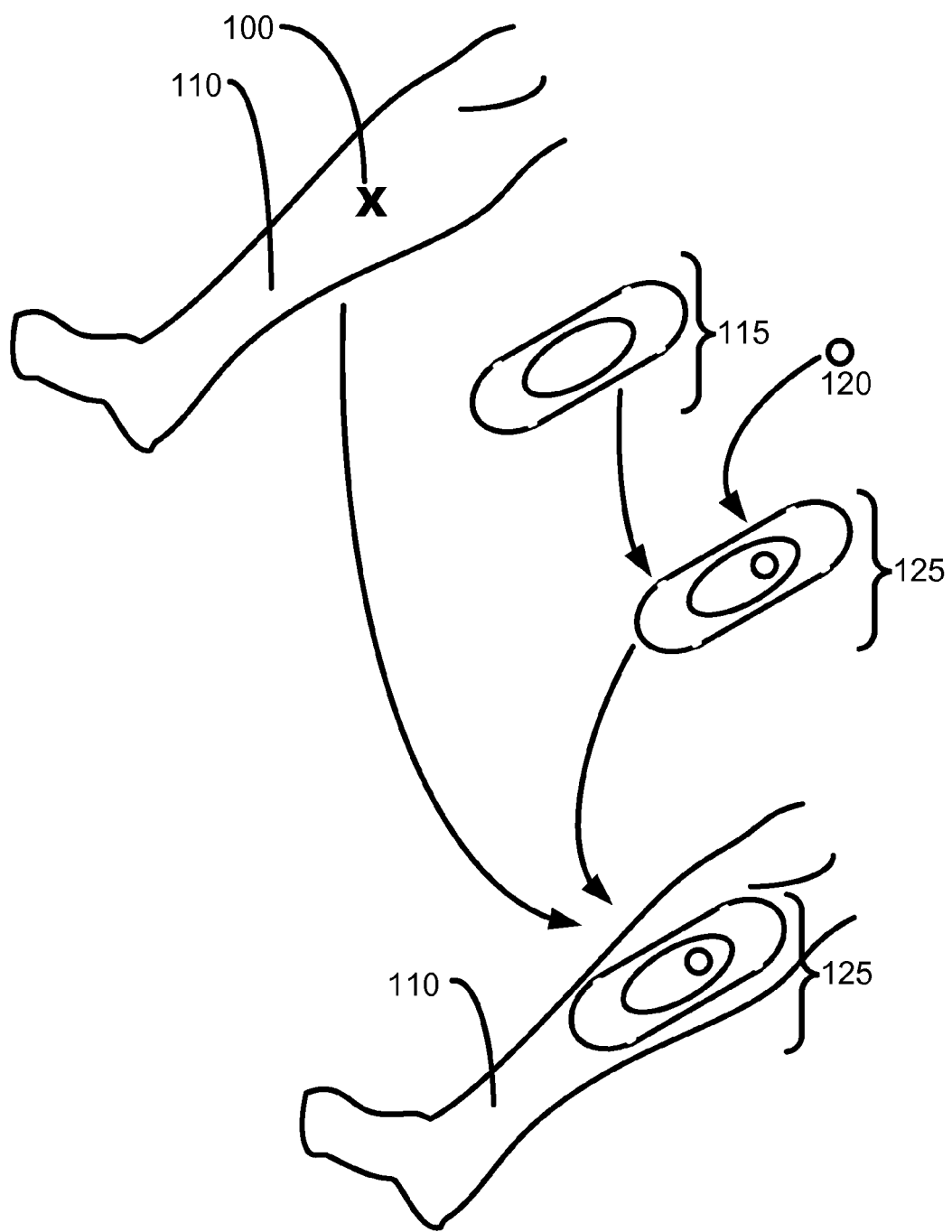
FIG. 1 is an illustration of an appurtenance to a wound dressing in use with a wound.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

The use of the same symbols in different drawings typically indicates similar or identical items unless context dictates otherwise.

With reference now to FIG. 1, shown is an illustration of an appurtenance to a wound dressing in use with a wound that may serve as a context for introducing one or more processes and/or devices described herein. As shown in FIG. 1, a body part 110, such as a leg, includes a wound 100. A wound dressing 115, selected by a medical caregiver as appropriate in size, shape and type for the wound 100, has an appurtenance 120 attached to generate an appurtenance affixed to a wound dressing combination unit, 125. The appurtenance 120 can be attached to the wound dressing 115 with a mechanical attachment. For example, a mechanical attachment can include attachments shaped like prongs, barbs, bristles, spikes, or spurs. The appurtenance 120 can be attached to the wound dressing 115 with a chemical attachment, such as a pressure-sensitive adhesive, a contact adhesive, or a quick-drying adhesive. The appurtenance 120 is a separate and distinct element that can be attached to the wound dressing 115 in a manner sufficient for operation during the use of a specific wound dressing 115. The appurtenance 120 is a separate and distinct element that can be attached to the wound dressing 115 in an irreversible manner. For example, the appurtenance-wound dressing combination unit, 125, can be disposed of after use. Immediate disposal after use can be desirable to minimize biosafety, contamination and biohazard issues. The appurtenance 120 is a separate and distinct element that can be attached to the wound dressing 115 in a reversible manner. For example, the appurtenance-wound dressing combination unit, 125, can be taken apart into its component wound dressing 115 and appurtenance 120 after use. For example, the appurtenance 120 can be configured for reuse with a new wound dressing 115. In some embodiments, an appurtenance includes modular elements suitable for reuse. For example some embodiments include one or more modular sensor units. The appurtenance 120 can be configured for reuse after treatment, such as after disinfection, cleaning, or sterilization. In some embodiments, an appurtenance 120 to a wound dressing 115 can be reused in whole or in part, for example, on a succession of wound dressings 115 used by the same patient.

The appurtenance 120 is configured for functional use only when attached to the wound dressing 115. The appurtenance 120 is designed to function only when attached to a wound dressing 115. The appurtenance 120 is of a size, shape and material for functional use only when attached to the wound dressing 115. The appurtenance 120 is configured to operate in conjunction with the wound dressing 115. The appurtenance 120 is appended to the wound dressing 115 to generate an appurtenance-wound dressing combination unit 125, as illustrated in the lower right region of FIG. 1. In some embodiments, the appurtenance 120 includes at least one region that projects into the structure of the wound dressing 115. In some embodiments, the region that projects into the structure of the wound dressing 115 is of a size and shape to be entirely enclosed within the structure of the wound dressing 115. In some embodiments, the region that projects into the structure of the wound dressing 115 is of a size and shape to project through the wound dressing 115, for example to a region adjacent to a wound. In some embodiments, the region that projects into the structure of the wound dressing 115 is of a size and shape to project through the wound dressing 115, for example to a wound bed region. In some embodiments, the region that projects into the structure of the wound dressing 115 is of a size and shape to project through a portion of the wound dressing 115, for example to a sinus or cavity of the wound bed. In some embodiments, the region that projects into the structure of the wound dressing 115 is of a size and shape to project through a portion of the wound dressing 115, for example to a dressing placed within a sinus or cavity of the wound bed. In some embodiments, the region that projects into the structure of the wound dressing 115 is of a size and shape to project through a portion of the wound dressing 115, for example to a layer placed adjacent to the wound surface. The appurtenance 120 affixed to the wound dressing 115 forms an integrated unit of the appurtenance and the wound dressing as a combination unit 125. In some embodiments, the wound dressing-appurtenance combination unit 125 is not readily separable, and the individual wound dressing 115 and appurtenance 120 are not suitable for separation and individual use after they have been joined together. As illustrated in the lower portion of FIG. 1, once the appurtenance 120 is affixed to the wound dressing 115, the appurtenance and the wound dressing together as a combination unit 125 are used to cover and monitor the wound 100. See also: U.S. patent application Ser. No. 13/445,174, "Appurtenances for Reporting Information Regarding Wound Dressings"; U.S. patent application Ser. No. 13/445,220, "Computational Methods and Systems for Reporting Information Regarding Appurtenances to Wound Dressings"; U.S. patent application Ser. No. 13/491,677, "Dormant to Active Appurtenances for Reporting Information Regarding Wound Dressings"; U.S. patent application Ser. No. 13/795,667, "Appurtenances to Cavity Wound Dressings"; and U.S. patent application Ser. No. 14/252,136, titled "Wound Dressing Monitoring Systems Including Appurtenances for Wound Dressings," filed on the same day as the instant application, which are all incorporated herein by reference.

In some aspects, an appurtenance 120 to a wound dressing 115 is configured to monitor one or more aspects of a wound 100. An appurtenance 120 to a wound dressing 115 can be used by a caregiver and/or a patient to monitor a wound 100. In some aspects, an appurtenance 120 to a wound dressing 115 is configured to monitor one or more aspects of a wound dressing 115. For example, in some embodiments an appurtenance is configured to monitor conditions within a wound dressing, such as from fluid interstitial to the fibers of the wound dressing. In some aspects, an appurtenance to a wound dressing is configured to monitor one or more aspects of a wound dressing environment. For example, in some embodiments an appurtenance to a wound dressing is configured to monitor one or more conditions directly adjacent to the wound dressing, for example at the surface of a wound dressing, and/or at a wound dressing-wound interface. For example, in some embodiments an appurtenance to a wound dressing is configured to monitor one or more conditions in a periwound region. For example, in some embodiments an appurtenance to a wound dressing includes a pressure sensor positioned to detect physical pressure at an interface between a wound dressing and a wound and/or adjacent skin region. For example, in some embodiments an appurtenance to a wound dressing includes a wetness sensor positioned to detect wetness at an interface between a wound dressing and a wound and/or adjacent skin region. For example, in some embodiments an appurtenance to a wound dressing is configured to monitor the interior conditions of a wound dressing, for example fluid saturation, temperature, physical pressure, and/or the presence of one or more specific biological molecules, such as one or more proteins or carbohydrates. In some embodiments an appurtenance to a wound dressing is configured to monitor the interior conditions of a wound dressing with one or more sensors and at least one transmission unit including circuitry configured to transmit information associated with the one or more sensor units. For example, fluid saturation within the fibers of some wound dressings can indicate that the dressing needs to be changed. For example, an excess temperature within a wound dressing can indicate inflammation and/or infection of the adjacent wound tissue in some circumstances. For example, physical pressure on or within the wound dressing can indicate swelling of the adjacent tissue, excess fluid within the wound dressing, and/or a constriction to the wound dressing that should be addressed. For example, the presence of one or more biological molecules specific to a bacterial species may indicate the presence of the bacteria species in the wound dressing propagated from an infection in the wound.

An appurtenance 120 to a wound dressing 115 can be used by a caregiver, including a patient, to monitor a wound dressing 115. An appurtenance 120 to a wound dressing 115 is configured to allow a user, such as a caregiver or patient, to monitor a wound dressing and the adjacent wound without disturbing the wound dressing 115 such as through removing the dressing 115 from the patient's wound 100. This approach, inter alia, improves comfort to the patient, reduces the chance of accidental infection in or contamination from uncovered wounds, and minimizes time requirements in wound care. In some aspects, an appurtenance 120 to a wound dressing 115 includes a transmitter that sends a signal to a device used by a caregiver or patient to monitor the wound dressing from the same room as the patient. In some aspects, an appurtenance 120 to a wound dressing 115 includes a transmitter that sends a signal to a device used by a caregiver remotely, such as through a pager, remote computing device, cell phone, or dedicated remote signaling device. The signal transmitter sends a signal containing information associated a wound and/or adjacent wound dressing such that a caregiver is able to receive, directly or indirectly, information relating to monitoring a wound and adjacent wound dressing at a distance from the patient, without disturbing the patient and with minimal time spent analyzing the wound 100 or wound dressing 115.

In some aspects, an appurtenance to a wound dressing is part of a system configured to automatically process and save information relating to an appurtenance and the related wound dressing to a medical record system, such as a medical records database. This automatic process reduces the potential for accidental loss or error in data entry regarding wound care, and reduces the time required by a caregiver in data entry into a record.

As shown in FIG. 1, the wound dressing with the affixed appurtenance combination unit 125 is used to cover the wound 100 on the body part 110. The wound dressing with the affixed appurtenance combination unit 125 can be secured to the body part 110 in a routine manner for the type of wound dressing 115 generally, such as through adhesive integral to the wound dressing 115 or with additional adhesive, wrappings, tapes or glues as generally applicable to the type of wound dressing 115 utilized in a given medical situation. Although not illustrated in FIG. 1, the wound dressing with the affixed appurtenance combination unit 125 can similarly be removed using standard removal procedures, such as with gentle pressure, gentle pulling, unwrapping, allowing it to loosen over time, or bio-compatible solvents. The appurtenances 120 described herein can be single-use and disposable along with the affixed wound dressing 115. In some embodiments, the appurtenances 120 described herein can be removed from a first wound dressing and then reconditioned in whole or in part, such as through cleaning or sterilization, and reused with a second wound dressing. In some embodiments, an appurtenance 120 can be reused for multiple wound dressings used on a single wound from a patient. The appurtenances 120 described herein are generally intended to be operable for the period of time a given wound dressing 115 is in use under standard conditions and time periods. After the wound dressing with the irreversibly affixed appurtenance combination unit, 125 is removed from the body part 110, it can be disposed of as a unit with routine disposal methods.

It is envisioned that the appurtenances described herein will be utilized while affixed to wound dressings over wounds of a variety of types, and operable to assist in the monitoring of wounds of a variety of types. For example, appurtenances can be used in conjunction with wound dressings to assist in monitoring acute wounds, such as those resulting from accidental injury or surgery. For example, appurtenances can be used in conjunction with wound dressings to assist in monitoring wounds closed by primary intention. For example, the appurtenances can be used to assist in monitoring wound dressings over surgical wounds, such as incisions and surgical stitches. For example, the appurtenances can be used to assist in monitoring wound dressings over acute wounds from injury, such as burn injuries, lacerations, or penetrating wounds. For example, appurtenances can be used in conjunction with wound dressings to assist in monitoring wounds closed by secondary intention. The appurtenances can also be used to assist in monitoring wound dressings over chronic wounds, such as those arising from chronic medical conditions and situations. For example, the appurtenances can be used to monitor the status of wound dressings covering venous leg ulcers, diabetic foot ulcers, pressure ulcers or arterial ulcers. See: "Advances in Wound Healing Techniques," publication D11A, Frost and Sullivan, 2008; "An Overview of Ulceration Wounds," Publication M4BB-54, Frost and Sullivan 2009; and "US Advanced Wound Care Market," Publication N71A-54, Frost and Sullivan 2010, which are each incorporated herein by reference. In some embodiments, appurtenances can be used in conjunction with wound dressings for oral wounds.

The appurtenances described herein can be useful in conjunction with an affixed wound dressing as a combination unit to monitor potential problems with a wound, such as excessive bleeding or other fluid formation that would be present in the wound dressing, or the presence of conditions in the dressing that indicate infection in an adjacent wound. See: Collier, "Recognition and Management of Wound Infections," *World Wide Wounds*, pages 1-9, (January 2004); Gray, "Assessment, Diagnosis and Treatment of Infection," *Wounds UK*, vol. 7, no. 2, supplement, (2011); and Mehmood et al., "Review Article: Applications of Modern Sensors and Wireless Technology in Effective Wound Management," *J Biomed Mater Res part B*, published online DOI: 10.1002/jbm.b.33063 (2013) which are each incorporated herein by reference. For example, some types of wound discharge can indicate infection. See, for example, Cutting and Harding, "Criteria for Identifying Wound Infection," *Journal of Wound Care*, vol. 3, no. 4, 198-201 (1994), which is incorporated herein by reference. The appurtenances as part of combination units 125 and related systems described herein can be used in conjunction with readily available types of wound dressings to monitor aspects of the affixed wound dressing, including parameters that indicate that a person should physically examine the wound dressing, such as excessive wetness, dryness, an elapsed period of time, or the presence of specific factors detected by one or more sensors of the appurtenance. The appurtenances as well as related systems described herein can be used in conjunction with readily available types of wound dressings to monitor aspects of the affixed wound dressing, including indications that the wound dressing should be changed (i.e. excessively wet, dry, or soiled).

The appurtenances described herein include transmission units configured to transmit signals, and thereby report information regarding the status of the affixed wound dressing or wound, to associated systems. The resulting information reporting can be used, in some embodiments, to supplement the medical record for a patient in an automated system and automatic process. The resulting information reporting can be used, in some embodiments, to automatically notify a caregiver that the status of the wound dressing has altered, indicating that a person should physically inspect the wound dressing.

As used herein, a caregiver includes at least one of a patient, a caregiver, and medical personnel. A caregiver can utilize some embodiments of the appurtenances and related systems described herein in relation with multiple types of wound dressings. Appurtenances can be fabricated in shapes and sizes to conform to a variety of standard wound dressing sizes, shapes and types. Appurtenances can be fabricated with, for example, transmission units, antennas and sensors appropriate for use with a variety of wound dressings. Appurtenances can be fabricated with, for example, transmission units, antennas and sensors appropriate for different medical situations and monitoring requirements. Appurtenances can be fabricated with, for example, one or more projections of a size, shape and material appropriate for use with a variety of wound dressings. While it is envisioned that every appurtenance will not be appropriate for use with every wound dressing (for example due to size, shape or material compatibility), a given appurtenance is expected to be suitable for use with a range of potential wound dressings. For example, a given appurtenance of a specific size, shape and fabrication, including type of transmission unit, sensors, and projection(s), should be suitable for use with a variety of wound dressings of conforming sizes, shapes and types. Generally, any specific appurtenance embodiment is not expected to only conform to use with a unique wound dressing of a specific size, shape and type. Instead, it is expected that a specific appurtenance embodiment will be suitable for use with a range of wound dressings. Similarly, it is expected that a specific appurtenance embodiment will be suitable for use with a range of wound and wound dressing monitoring requirements.

In the attached drawings, an appurtenance 120 is often illustrated as affixed to an outer surface of a wound dressing 115, for example an outer surface distal to a surface of the body part 110 adjacent to the wound 100. However, in some embodiments, an appurtenance 120 can be configured to attach to one or more surfaces of a wound dressing 115 adjacent to a surface of the body part 110 adjacent to the wound 100. For example, in embodiments wherein an appurtenance 120 is configured to be attached to a wound dressing 115 of a substantially rectangular, ovoid, or raised conformation, an appurtenance 120 can be configured to be attached to a side surface of the wound dressing 115. For example, in embodiments wherein an appurtenance 120 is configured to be attached to a wound dressing 115 with an unusually strong or thick outer cover layer, the appurtenance 120 can be configured to attach to an underside of the wound dressing 115. In some embodiments, an appurtenance is configured to attach to a surface of a wound dressing 115 in contact with the surface of the body part 110.

For example, the appurtenances described herein can be configured to be affixed to a dry gauze dressing, which may or may not include an outer cover layer. For example, the appurtenances described herein can be configured to be attached to a dry silicone or other solid foam dressing, which may or may not include an outer cover layer. For example, the appurtenances described herein can be configured to be affixed to a wound dressing used to close a small or thin wound or surgical incision, such as a butterfly dressing (e.g. SteriStrip™ adhesive strips, available from Nexcare™, part of 3M Corporation). For example, appurtenances such as those described herein can be configured to be affixed to a dressing configured to maintain moisture or other materials adjacent to the wound surface. For example, appurtenances such as those described herein can be configured to be used with hydrogel wound dressings, for example Aquaflo™ Hydrogel Wound Dressing by Kendall Corporation, or Elasto-Gel™ Hydrogel Occlusive Dressing by Southwest Technologies. For example, appurtenances such as those described herein can be affixed to wound dressings including hydrocolloids, for example DuoDERM CGF Sterile Hydrocolloid Dressing manufactured by DuoDERM Corporation. For example, appurtenances such as those described herein can be configured to be used with wound dressings containing one or more medicinal agents, such as antibiotics. For example, appurtenances such as those described herein can be used with wound dressings impregnated with PHMB (Polyhexamethylene Biguanide), such as Telfa™ A.M.D. antimicrobial wound dressings, manufactured by Kendall Corporation. For example, appurtenances such as those described herein can be configured to be used with wound dressings including ionic silver, such as Maxorb™ Extra Ag wound dressings manufactured by Medline Corporation. Appurtenances such as those described herein can be configured to be affixed to wound dressings over wounds wherein the tissue of the wound is being directly monitored using other devices, for example as described in U.S. Pat. No. 6,963,772 to Bloom et al., titled "User-retainable Temperature and Impedance Monitoring Methods and Devices," which is incorporated herein by reference. Appurtenances such as those described herein can be configured to be affixed to wound dressings over wounds wherein the patient is being directly monitored using other devices, for example as described in U.S. Pat. No. 7,030,764 to Smith and Cooper, titled "Apparatus and Method for Reducing the Risk of Decubitus Ulcers;" U.S. Pat. No. 7,297,112 to Zhou et al., titled "Embedded Bio-Sensor System;" U.S. Pat. Nos. 7,372,780, 8,014,234 and U.S. Pat. No. 7,813,226 to Braunberger, titled "Timing System and Device and Method for Making the Same;" U.S. Pat. No. 7,666,151 to Sullivan et al., titled "Devices and Methods for Passive Patient Monitoring;" U.S. Pat. No. 7,703,334 to Cochran, titled "Bandage Type Sensor Arrangement and Carrier Assembly Therefore, and Method of Manufacture;" and International Patent Publication No. WO 2005/009328 to Nikolic, titled "ABT-Anti-Bedsore Timer," which are each incorporated herein by reference. Appurtenances such as those described herein can also be used in conjunction with a system to monitor assets within a health care facility, for example as described in US Patent Application No. 2007/0247316 to Wildman et al., titled "Article Locating and Tracking Apparatus and Method," which is incorporated herein by reference.

Wound dressings such as those described herein are generally used for a relatively short period of time, on the order of hours or days, and then removed for disposal. Similarly, a wound dressing with an affixed appurtenance combination unit should be configured for use over the course of hours or days and then removed and disposed of using standard methods. A wound dressing with an affixed appurtenance is single use and disposable after use. For example, a caregiver can require a new wound dressing every 24 hours (1 day) for an acute wound. Any wound dressing utilized in this type of situation would, consequently, be of a size and shape to remain affixed to the wound region over the course of at least a 24 hour period and then removed for disposal. An appurtenance to a wound dressing intended for use over the course of a 24 hour time period, similarly should be of a size, shape, material fabrication, and capabilities to function while affixed to the wound dressing over the 24 hour period that the dressing is in use. As an additional example, a caregiver can decide that for another type of wound, such as a chronic wound, the wound dressing needs to be removed and replaced once every 3 days, or every 4 days, or every 5 days, or every 6 days, or every 7 days. Correspondingly, an appurtenance affixed to a wound dressing intended for use over the course of at least 3 to 7 days should be of a size, shape, material fabrication, and capabilities to function while affixed to the wound dressing over at least the 3 to 7 day period that the dressing is in use. In embodiments wherein an appurtenance is intended for reuse, such as reuse on a second or subsequent wound dressing used over a wound, the appurtenance should be of a size, shape, material fabrication and capabilities to function during the entire intended use, including the time period of removal from a first wound dressing and application to a second wound dressing, as well as any intermediate refurbishment or cleaning process.

In some embodiments, an appurtenance to a wound dressing includes: a substrate with at least one surface of a size and shape to mate with a surface of a wound dressing; a plurality of projections attached to the substrate and positioned to secure the substrate to the wound dressing; one or more sensor units attached to the substrate, the one or more sensor units configured to sense a condition of the wound dressing; and a transmission unit attached to the substrate and operably coupled to the one or more sensor units, the transmission unit including circuitry configured to transmit information associated with the one or more sensor units.

Figure 2:
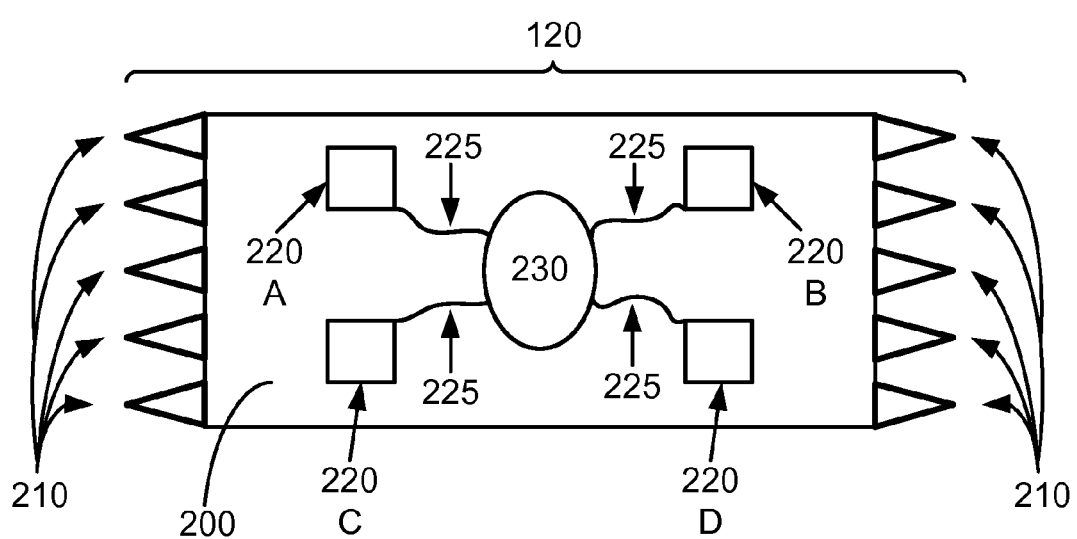
FIG. 2 is a schematic of an appurtenance to a wound dressing.

FIG. 2 depicts aspects of an embodiment of an appurtenance 120. The embodiment of an appurtenance 120 shown in FIG. 2 includes a substrate 200 that is a substantially planar structure. The appurtenance 120 in FIG. 2 is depicted to illustrate aspects of one of the largest faces of the appurtenance, or an approximately "top-down" view of the appurtenance as it might be used in conjunction with a wound dressing. The embodiment illustrated in FIG. 2 includes sensor units 220 A, 220 B, 220 C and 220 D attached to the substrate. Some embodiments include one sensor unit. Some embodiments include two, three, four, five or more than five sensor units. In some embodiments, the one or more sensor units attached to the substrate are directly attached to the substrate. In some embodiments, the one or more sensor units attached to the substrate are indirectly attached to the substrate, such as within a frame or similar structure with reversible fasteners for sensor units that are modules. In some embodiments, the one or more sensor units are attached to the substrate within an interior region of the substrate. For example, the substrate can include two or more walls and one or more sensor units can be affixed within a region between the walls. For example, the substrate can include two or more planar sheets and one or more sensor units can be affixed within a region between the planar sheets. The plurality of sensor units 220 A, 220 B, 220 C and 220 D are collectively referred to as "sensor units 220" with reference to the figures herein. In the embodiment of FIG. 2, the appurtenance 120 includes a plurality of sensor units 220, or four sensor units. The sensor units 220 are positioned approximately in the middle of each of the four quadrants of the substantially rectangular substrate 200 in the embodiment shown in FIG. 2. Some embodiments include at least one wire connector positioned between each of the one or more sensor units and the transmission unit. Each of the sensor units 220 illustrated in FIG. 2 is connected to a transmission unit 230 with a wire connector 225. Aspects of the appurtenance that are illustrated in FIG. 2 may be covered up or obscured in some embodiments. For example, in some embodiments an appurtenance includes a cover that would obscure sensor units 220 A, B, C, D and transmission unit 230 as well as associated wire connectors 225.

The appurtenance 120 shown in FIG. 2 includes a first end with a first set of the plurality of projections 210 attached to the first end of the substrate 200, and a second end, with a second set of the plurality of projections 210 attached to the second end of the substrate 200. In the view shown in FIG. 2, the left side of the appurtenance 120 can be considered as a "first end" and the right side of the appurtenance 120 can be considered as a "second end" for purposes of illustration. The plurality of projections 120 are collectively referred to as "projections 210" with reference to the figures herein. The projections 210 are each substantially conical structures, with a wide end affixed to the end of the substrate 200 and a narrow end desiccant positioned distal to the substrate 200. In some embodiments, each of the projections 210 include a proximal end and a distal end, with the projections 210 tapering in size from the proximal end to the distal end. In some embodiments, the plurality of projections extend outward along a largest linear dimension of the substrate. For example, in the embodiment shown in FIG. 2, the projections extend outward in substantially the same plane as the largest plane of the substrate.

Depending on the embodiment, the projections can project in one or more directions substantially away from the surface of the appurtenance configured to conform with an outer surface of the wound dressing, or angle in a direction substantially perpendicular to the surface configured to conform with an outer surface of the wound dressing of the appurtenance. Some embodiments include at least one projection which is curvilinear. Some embodiments include at least one projection which is a composite shape. In embodiments including one or more projections that are not substantially straight, an angle (e.g. θ) of the projection can be determined by the angle formed at the base of the projection immediately adjacent to the surface of the appurtenance configured to conform with an outer surface of the wound dressing.

A projection can be a substantially hollow tubular structure. A substantially hollow tubular structure of a projection can include an opening on the distal end of the projection. In some embodiments projections can be of different shapes and conformations. For example, a projection can be solid, tubular, conical, cylindrical, tapered, curved, angular or other shape or combination of shapes as appropriate to the specific embodiment. Embodiments including a plurality of projections can include projections of different sizes and shapes. A projection can be substantially straight and form a substantially linear internal channel, or it can be curved and form a substantially curvilinear internal channel. The drawings illustrated herein are not to scale. The drawings illustrated herein represent relationships and shapes of the items described. Although not expressly illustrated herein, a projection can be relatively large relative to the total size of the appurtenance. For example, the volume of a projection or a group of projections attached to an appurtenance can be 51%, 55%, 60%, 65%, 70%, 75%, 80%, 85%, 90%, 95% or 100% of the volume of the portion of the appurtenance configured to conform with an outer surface of a wound dressing. Similarly, a projection can be relatively small relative to the total size of the appurtenance. For example, the volume of a projection or a group of projections attached to an appurtenance can be 49%, 45%, 40%, 35%, 30%, 25%, 20%, 15%, 10%, or 5% of the volume of the portion of the appurtenance configured to conform with an outer surface of a wound dressing. In some embodiments, a projection is located at an edge region of the substantially planar region of the appurtenance, and in some embodiments a projection is located substantially centrally to the planar surface of the appurtenance configured to conform with an outer surface of the wound dressing. In some embodiments, a substantially planar appurtenance includes at least one projection wherein the entire appurtenance is of a size and shape to be secured against an external surface of a wound dressing with force, for example from a human thumb or finger.

In some embodiments, an appurtenance can be fabricated with one or more regions configured for the attachment of different modules. In some embodiments, an appurtenance includes modules that are configured for removal and replacement. For example, some embodiments include appurtenances with removable and replaceable sensor units. During fabrication, a basic appurtenance structure can be utilized and different specific modules added as desired in a particular embodiment. For example, an appurtenance can be fabricated with at least one region configured to attach a projection. For example, a region configured to attach a projection can include a region with a surface conforming to an outer surface of the projection. For example, a region configured to attach a projection can include a conduit configured to align with the hollow interior of the projection. The region of the appurtenance configured to attach a projection can be configured for attachment of different projection types, depending on the embodiment. For example, the region of the appurtenance configured to attach a projection can be configured for attachment of projections of different lengths or different materials as desired in the construction of a particular embodiment. In some embodiments, an appurtenance can have multiple regions configured for attachment of multiple projections of different types. In some embodiments, an appurtenance can have one or more removable antenna modules. In some embodiments, an appurtenance can have one or more removable sensor unit modules. For example, an appurtenance can have one or more removable power source modules, such as batteries or solar cells. In some embodiments, a module can include a spacer element, or a component configured to assist in physically positioning one or more other modules.

In some embodiments, an appurtenance includes a barrier layer, such as a thin film, positioned between the substrate of the appurtenance and one or more modules of the appurtenance. See: U.S. Pat. No. 7,914,867, "Medical Gas Barrier Film and Medical Bag Using the Same" to Mori et al.; and U.S. Pat. No. 5,939,205 "Gas Barrier Resin Film" to Yokoyama et al., which are each incorporated by reference. In some embodiments, an appurtenance includes a barrier layer, such as a thin film, positioned between the enclosure of the appurtenance and one or more modules of the appurtenance. The barrier layer can be positioned, for example, between the substrate of an appurtenance and one or more removable and replaceable modules, such as sensor units. The barrier layer can, for example, reduce the possibility of biological contamination spread within an appurtenance, or between components of an appurtenance, such as between sensor units. In some embodiments, a barrier layer is positioned within an interior region of an enclosure of an appurtenance, for example adjacent to an interior surface of the enclosure. In some embodiments, a barrier layer is positioned within an interior region of an enclosure of an appurtenance, for example affixed to an interior surface of the enclosure. A barrier layer can be positioned to reduce the potential for contamination of a modular component of an appurtenance, for example partially or entirely surrounding a removable sensor unit.

In some embodiments, an appurtenance includes a fluid control material, such as a fluid control film, positioned to permit directional flow of a liquid from a position external to the appurtenance to an internal region of the appurtenance, such as a position adjacent to a sensor unit. See U.S. Pat. No. 6,420,622 to Johnston et al. "Medical Article Having Fluid Control Film," which is incorporated herein by reference. For example, some embodiments include a fluid control film within a conduit or aperture in a substrate of an appurtenance, the fluid control film positioned to direct fluid flow from a wound dressing into an interior region of the substrate, such as through an internal conduit and/or to a sensor unit. For example, some embodiments include a fluid control film within a conduit or aperture in an enclosure of an appurtenance, the fluid control film positioned to direct fluid flow from a wound dressing into an interior region of the enclosure, such as to a sensor unit. For example, some embodiments include a fluid control film within a conduit or aperture in a projection of an appurtenance, the fluid control film positioned to direct fluid flow from a wound dressing through an interior region of the projection and to a connected sensor unit. For example, some embodiments include a fluid control film within a conduit or aperture in a projection of an appurtenance, the fluid control film positioned to direct fluid flow from a wound dressing through an interior region of the projection and to a connected transmission unit. In some embodiments, an appurtenance includes a fluid control film positioned to permit directional flow of a liquid from a position external to the appurtenance to an internal region of the appurtenance, such as a position adjacent to a sensor unit.

An appurtenance can be fabricated from a variety of materials, as appropriate to an embodiment. An appurtenance can be fabricated, for example, substantially from a plastic material. For example, a structural portion, such as a substrate, enclosure, shell or base can be fabricated from a plastic material. For example, one or more projections can be fabricated from a plastic material. An appurtenance can be fabricated, for example, from one or more acrylics, polyesters, silicones, polyurethanes and/or halogenated plastics. An appurtenance can include one or more projections fabricated, for example, from one or more plastic materials. An appurtenance can include one or more projections fabricated, for example, from one or more acrylics, polyesters, silicones, polyurethanes and/or halogenated plastics. An appurtenance can be fabricated from one or more bio-compatible materials, for example bio-compatible plastics, resins, epoxies and metals. An appurtenance can be fabricated from one or more materials to achieve a level of flexibility of the appurtenance relevant to a specific use, for example an appurtenance can be fabricated from substantially rigid materials or substantially flexible materials, or a combination thereof to achieve a particular flexibility of an appurtenance as required for a specific embodiment. An appurtenance can be fabricated from one or more composite materials, such as plastic with an overlay of epoxy or plastic with an overlay of one or more metals. An appurtenance including a transmission unit can include, for example, one or more metal components, for example as circuitry or as one or more antennas. An appurtenance including a transmission unit can include, for example, stainless steel, copper or zinc alloy. An appurtenance can be fabricated from one or more ceramic materials, such as within a transmission unit. Generally, it is envisioned that materials with low weight will be suitable for a variety of appurtenance embodiments, so as to reduce weight and associated physical stress on a wound dressing. Similarly, it is envisioned that materials with sufficient strength and toughness to be fabricated into small and thin components will be desirable for fabrication of appurtenance embodiments. As the appurtenances are to be affixed to wound dressings, bio-compatible materials can be preferred. As the appurtenances are to be affixed to wound dressings and, in some embodiments, disposed of with the wound dressings, materials that do not require special handling or disposal are preferable in most embodiments.

In some embodiments, the appurtenance includes a substrate or enclosure that is configured to attach to the wound dressing. For example, the substrate or enclosure can be configured as a support for other features of the appurtenance. In some embodiments, the substrate includes a substantially planar structure wherein the area of surface is less than the area of the wound dressing. In some embodiments, the substrate or enclosure is configured to irreversibly attach directly to an external surface of the wound dressing. In some embodiments, the substrate or enclosure includes an adhesive on a surface conforming to an external surface of the wound dressing. For example, the surface conforming to an external surface of a wound dressing can include a glue, epoxy, sealant, mucilage, paste or other binder material. In some embodiments, the substrate or enclosure includes at least one chemical adherent positioned to affix the substrate or enclosure to a wound dressing. In some embodiments, the surface of the substrate or enclosure conforming to an external surface of a wound dressing can include an adhesive covered by a removable protective sheet configured for detachment and exposure of the adhesive when the appurtenance is attached to the wound dressing. In some embodiments, the surface of the substrate or enclosure of the appurtenance configured to conform with an outer surface of the wound dressing can include barbs, hooks, pins, prongs or other extensions configured to adhere or fix into the outer surface of the wound dressing. In some embodiments, the surface of the substrate or enclosure of the appurtenance configured to conform with an outer surface of the wound dressing can include a mixture or combination of any of the above.

In some embodiments, the substrate or enclosure of an appurtenance includes a flexible material. For example, the substrate or enclosure of an appurtenance can include a pliable plastic, a woven fabric material, soft mesh or other flexible material. In some embodiments, the substrate or enclosure of an appurtenance includes a rigid material. For example, the substrate or enclosure of an appurtenance can include at least one rigid plastic material in a location configured to provide support for a portion of the appurtenance. For example, the substrate can include at least one rigid plastic material at a location configured to attach a projection, the rigid plastic configured to provide physical support for the attached projection. In some embodiments, the substrate or enclosure of an appurtenance includes at least one bio-compatible material. For example, the substrate or enclosure of an appurtenance can include one or more bio-compatible plastic materials, one or more bio-compatible fabric materials, or one or more bio-compatible metals.

In some embodiments, an appurtenance to a wound dressing is substantially sterilized prior to use and the appurtenance is fabricated from materials that are known to be stable under the expected sterilizing conditions. For example, the appurtenance can be treated with one or more chemical disinfectants or UV surface radiation for a period of time sufficient to substantially sterilize the appurtenance prior to use. For example, the appurtenance can be treated with one or more antimicrobial gasses, for example ethylene oxide (ETO), prior to use. For example, the appurtenance can be treated with a chemical sterilizing agent, such as hydrogen peroxide in liquid or vapor form, prior to use. For example, the appurtenance can be treated with steam as an anti-infective prior to use. For example, the appurtenance can be treated with heat prior to use. For example, the appurtenance can be treated with gamma irradiation prior to use. For example, the appurtenance can be treated with electron irradiation prior to use. In some embodiments, one or more components of an appurtenance, for example a sensor unit, a substrate, or an enclosure, are fabricated from one or more materials known to be physically stable after multiple sterilizing treatments. In some embodiments, an appurtenance to a wound dressing includes a sterile wrapper. For example, an appurtenance to a wound dressing can be stored and/or transported within a sterile wrapper, such as a firm paper wrapper or a plastic film. A sterile wrapper configured for storage and/or transport of an appurtenance can be treated to minimize contamination, for example coated with one or more anti-microbial agents.

Appurtenances include one or more sensor units. Each sensor unit includes at least one sensor. In some embodiments, a sensor unit includes more than one sensor, for example, two sensors, three sensors or four sensors in a single sensor unit. A sensor unit can include, for example, two or more sensors of a specific type. A sensor unit can include, for example, two or more sensors wherein each of the sensors is configured to sense a different parameter, for example including different antibodies or aptimers configured to bind with distinct target proteins. Sensor units can include sensors specific for detection of specific proteins, or related protein families (e.g. MMPs). A sensor unit can be configured to detect one or more conditions of a wound dressing, such as temperature, pressure, fluid saturation, and/or fluid level within the interior of the wound dressing. A sensor unit can be configured to detect one or more biological molecules present in a wound dressing, such as biological molecules arising from one or more bacteria, biological molecules arising from one or more viruses, biological molecules arising from the wound, and/or biological molecules arising from tissue adjacent to the wound.

A variety of sensors can be utilized in different embodiments of the appurtenances, depending on factors such as the intended use of the appurtenance, size, weight, cost, biocompatibility, safety and ease of disposal. "Sensors," as used herein, can be of a variety of types depending on the embodiment. One or more sensors can include a chemical sensor. For example, one or more sensors can include a sensor that relies on a chemical change, such as a chemical reaction, as part of the detection process. One or more sensors can include at least one sensor responsive to changes in capacitance, or a measure of the ability of a configuration of materials to store electric charge. A general review of biosensors that detect changes in the dielectric properties of an electrode surface can be found in Berggren et al., "Capacitive Biosensors," *Electroanalysis* vol. 13, no. 3, 173-180, (2001), which is incorporated herein by reference. For example, one or more sensors can include a micromechanical biosensor with a fixed-fixed beam attached to an interdigitated capacitor (see, for example, Lim et al., "A Micromechanical Biosensor with Interdigitated Capacitor Readout," *Proceedings of the* 2011 *IEEE/ICME International Conference on Complex Medical Engineering*, May 22-25, Harbin, China, which is incorporated herein by reference). Sensors can also include nanowire nanosensors, for example as described in Cui et al., "Nanowire Nanosensors for Highly Sensitive and Selective Detection of Biological and Chemical Species," *Science*, vol. 293, 1289-1292 (2001), which is incorporated herein by reference. Sensors can include those utilizing antibodies secured to a graphene substrate. See Tehrani et al., "Detection of Monoclonal Antibodies using Chemically Modified Graphite Substances," *IEEE Sensors* 2010 *Conference Proceedings*, 428-431, (2010), which is incorporated herein by reference. In some embodiments, sensors include aptamer-modified graphene field-effect transistors, see Ohno et al., "Graphene Field-Effect Transistors for Label-Free Biological Sensors," *IEEE Sensors* 2010 *Conference Proceedings*, 903-906, (2010), which is incorporated herein by reference. A sensor in an appurtenance can interact with a sensor present in a wound dressing, for example as described in U.S. Pat. No. 6,283,938 to McConnell, titled "Medicating Bandage and Controllable Permeable Membrane," which is incorporated herein by reference. A sensor can include a field effect transistor (FET), such as described in U.S. Pat. No. 7,507, 675 to Zuilhof et al., titled "Device Manufacturing Method and Device," which is incorporated herein by reference. A sensor can include a nano-cantilever device, such as described in U.S. Pat. No. 7,612,424 to Espinosa and Ke, titled "Nanoelectromechanical Bistable Cantilever Device," which is incorporated herein by reference. In some embodiments, sensors include temperature sensors, which can be included in the sensor units along with a different type of sensor (e.g. a micromechanical biosensor). In some embodiments, sensors include moisture sensors, positioned to detect the level of moisture present in a wound dressing. A moisture sensor can include, for example, a capacitance-based moisture sensor. In some embodiments, sensors include resonance sensors, positioned to detect changes in resonance of a sensor unit in proximity to a wound dressing relative to the amount of fluid in the wound dressing (i.e. the "wetness" of the dressing). In some embodiments, sensors include resonance sensors, positioned to have altered internal resonance, such as within a cavity resonator of the sensor, relative to the fluid saturation of the wound dressing.

In some embodiments, a sensor unit includes a pressure sensor. For example, a pressure sensor can be positioned to detect the physical pressure on a wound dressing, such as from swelling of the dressing or against the surface of the dressing. In some embodiments, sensors include pressure sensors, positioned to detect physical pressure on the wound dressing from an external source, such as a bandage wrap or cover. In some embodiments, sensors include pressure sensors, positioned to detect physical pressure in the interface between a surface of the wound dressing and the wound and/or adjacent skin of the patient. In some embodiments, a sensor unit includes a temperature sensor. In some embodiments, a sensor unit includes both a pressure sensor and a temperature sensor. See, for example, DeHennis and Wise, "A Wireless Microsystem for the Remote Sensing of Pressure, Temperature, and Relative Humidity," *Journal of Microelectromechanical Systems*, 14(1): 12-22 (2005), which is incorporated by reference herein. In some embodiments, a sensor unit includes a sensor configured to detect one or more aspects of a fluid within the wound dressing and/or positioned adjacent to the wound dressing. In some embodiments, a sensor unit includes a sensor configured to detect one or more aspects of a gas within the wound dressing or positioned adjacent to the wound dressing. In some embodiments, a sensor unit includes a pH sensor. In some embodiments, a sensor unit includes a detector of a specific chemical, such as nitric oxide. In some embodiments, a sensor unit includes a detector of a specific biological agent, such as a bacterial protein. In some embodiments, a sensor unit includes a sensor including at least one aptimer. In some embodiments, a sensor unit includes a sensor including at least one antibody. In some embodiments, a sensor unit includes a plurality of sensors within the sensor unit. Some embodiments include a sensor unit including: a sensor; circuitry for accepting data from the sensor; circuitry for processing the accepted data; and circuitry for sending the processed data to the transmission unit. Some embodiments include a sensor unit with reversible fasteners of a size and shape for attachment to the substrate. For example, an appurtenance can be configured to attach one or more modular sensor units.

Some sensors within sensor units such as those described herein can be configured to sense fluids. Some sensors within sensor units such as those described herein can be configured to sense one or more components of a fluid. Some sensors within sensor units such as those described herein can be configured to sense one or more analytes within a fluid. As used herein, fluid includes both gasses and liquids individually or as mixtures. Some sensors within sensor units described herein can detect fluids, whether in gaseous state or liquid state. If the fluid is a liquid, it can be drawn into an appurtenance through capillary action. If the fluid is a gas, it can be drawn into the appurtenance through gravity (i.e. where the appurtenance is oriented on the top of a wound dressing over a wound). In some embodiments, the appurtenance includes a micropump positioned to move fluids through a projection and into the appurtenance in a position adjacent to a sensor within a sensor unit. In some embodiments, the appurtenance includes a desiccant material in fluid communication with the wound dressing. In some embodiments, the appurtenance includes a desiccant material positioned to draw fluid from a wound dressing into an interior of the appurtenance and to a sensor of a sensor unit. For example, a desiccant material can be positioned, in some embodiments, within a conduit or channel within an appurtenance. For example, a desiccant material can be positioned, in some embodiments, within a dedicated chamber attached to a sensor unit. In some embodiments, the appurtenance includes a sealed chamber that is under vacuum and connected to a projection or aperture. When the seal is broken, it sucks up the fluid into the tube in response to the low (or negative) air pressure in the tube.

In some embodiments, one or more sensor units include: one or more sensors; circuitry for accepting data from the one or more sensors; circuitry for processing the accepted data; and circuitry for sending the processed data to the transmission unit. In some embodiments, one or more sensor units include reversible fasteners of a size and shape for attachment to a substrate. In some embodiments, one or more sensor units include reversible fasteners of a size and shape for attachment to an enclosure. For example, reversible fasteners can include pins, clips, screws or other fasteners of a size and shape to mate with an internal surface of a substrate or an enclosure of an appurtenance.

A "transmission unit," as used herein, can be one or more of a variety of units that are configured to send and/or receive signals, such as signals carried as electromagnetic waves. In embodiments where the appurtenance includes a substrate, the transmission unit can be attached to a surface of the substrate, the transmission unit including circuitry and at least one antenna operably attached to the circuitry, the transmission unit configured to transmit a signal. In embodiments where the appurtenance includes an enclosure, the transmission unit can be attached to a surface of the enclosure, the transmission unit including circuitry and at least one antenna operably attached to the circuitry, the transmission unit configured to transmit a signal. A transmission unit generally includes at least one antenna and associated circuitry. A transmission unit can include a transmitter and a receiver. A transmission unit can include volatile or nonvolatile memory. A transmission unit can include a processor. A transmission unit can be operably connected to an energy source, such as a battery. In some embodiments of an appurtenance, it is desirable to include a self-compensating antenna, such as described in U.S. Pat. No. 7,055,754 to Forster, titled "Self-Compensating Antennas for Substrates having Differing Dielectric Constant Values," which is incorporated herein by reference. A transmission unit can be operably connected to a processor. A transmission unit can be operably connected to a sensor. A transmission unit can be configured to transmit a signal in response to an interrogation signal. A transmission unit can include an energy harvesting unit, such as a unit configured to obtain energy from electromagnetic waves. A transmission unit can include a transponder utilizing electromagnetic waves, for example as described in "Fundamental Operating Principles," in Chapter 3 of the *RFID Handbook: Fundamentals and Applications in Contactless Smart Cards and Identification*, Klaus Finkenzeller, John Wiley & Sons, (2003), which is incorporated herein by reference. A transmission unit can include an oscillator and encoder configured to generate a programmable pulse position-modulated signal in the radio frequency range. See, for example, U.S. Pat. No. 4,384,288 to Walton, titled "Portable Radio Frequency Emitting Identifier," which is incorporated herein by reference. A transmission unit can include a radio frequency identification device (RFID). A transmission unit can be configured to be a transmitter of signals in the UHF range. A transmission unit including an RFID device can be configured to transmit signals in the UHF standard range utilized in a global region, as illustrated in the "Worldwide RFID UHF Map" by Intelleflex Corporation (©2009), which is incorporated herein by reference. A transmission unit can include a radio frequency identification device (RFID), which can be a passive RFID device, a semi-passive RFID device, or an active RFID device, depending on the embodiment. See, for example, Chawla and Ha, "An Overview of Passive RFID," *IEEE Applications and Practice*, 11-17 (September 2007), which is incorporated herein by reference. A transmission unit can include a battery-assisted passive RFID device, such as sold by Alien Technology®, Morgan Hill, Calif., such as described in the brochure from Alien Technology® titled "Battery Assisted Passive Tags" and incorporated herein by reference. A transmission unit can include an optical transmission unit. A transmission unit can be configured to transmit at approximately 13.56 megahertz (MHz), or within the ISO 14443 standard parameters. See Patauner et al., "High Speed RFID/NFC at the Frequency of 13.56 MHz," presented at the *First International EURASIP Workshop on RFID Technology*, pages 1-4, 24-25 Sep. 2007, Vienna Austria, which is incorporated herein by reference. A transmission unit can include at least two antennas. A transmission unit can include a self-compensating antenna system. An antenna can include dielectric material configured to electrically interact with one or more antennas. See, for example, U.S. Pat. No. 7,055,754 to Forster, titled "Self-Compensating Antennas for Substrates Having Differing Dielectric Constant Values," which is incorporated herein by reference. A transmission unit can include a hybrid backscatter system configured to function in an RFID, IEEE 802.11x standard and Bluetooth system. See, for example, U.S. Pat. No. 7,215,976 to Brideglall, titled "RFID Device, System and Method of Operation Including a Hybrid backscatter-based RFID Protocol Compatible with RFID, Bluetooth and/or IEEE 802.11x Infrastructure," which is incorporated herein by reference. A transmission unit can be configured to transmit at approximately 131 kilohertz (KHz), for example as part of a RuBee™ (IEEE standard 1902.1) system (sold, for example, by Visible Assets™, Inc.). See for example: the description of RuBee™ systems from the Visible Assets™ webpage; Stevens et al., "RuBee (IEEE 1902.1)—The Physics Behind, Real-Time, High Security Wireless Asset Visibility Networks in Harsh Environments," a white paper from Visible Assets™; and in US Patent Application No. 2007/0171076 to Stevens and Waterhouse, titled "Low-frequency Radio Tag Encapsulating System," each of which are incorporated herein by reference. A transmission unit can include a near field communication (NFC) device. A transmission unit can include a Wireless Identification and Sensing Platform (WISP) device, manufactured by Intel Corporation, such as described in the "WISP: Wireless Identification and Sensing Platform" webpage (downloaded on Oct. 28, 2011) incorporated herein by reference. A transmission unit can be operably coupled to a sensor, such as a sensor that detects changes in capacitance (see, e.g. Sample et al., "A Capacitive Touch Interface for Passive RFID Tags," 2009 *IEEE International Conference on RFID*, 103-109 (2009), which is incorporated herein by reference). A transmission unit can be operably coupled to a sensor, such as described in: Ruhanen et al., "Sensor-enabled RFID Tag and Handbook," from *Building Radio Frequency Identification for the Global Environment* (2008); Sample et al., "Design of an RFID-Based Battery-Free Programmable Sensing Platform," *IEEE Transactions on Instrumentation and Measurement*, vol. 57, no. 11, 2608-2615 (2008); Yeager et al., "Wirelessly-Charged UHF Tags for Sensor Data Collection," 2008 IEEE International Conference on RFID, Apr. 16-17, 2008, pages 320-327; U.S. Pat. Nos. 5,904,671 and 6,348,640 to Navot and Botton, each titled "Tampon Wetness Detection System;" U.S. Pat. No. 7,446,660 to Posamentier titled "Passive Environmental RFID Transceiver;" and U.S. Pat. No. 5,704,352 to Tremblay and Buckles, titled "Implantable Passive Bio-Sensor," which are each incorporated herein by reference. A transmission unit can be operably coupled to a data storage unit, for example as described in U.S. Pat. No. 7,825,776 to Smith and Haehnel, titled "Device Configuration with RFID," and US Patent Application No. 2009/0243813 to Smith at al., titled "Wireless Programming of Non-Volatile Memory with Near-Field UHF Coupling," which are each incorporated herein by reference.

In some embodiments, the transmission unit can include an acoustic transmitter. For example, a transmission unit can include a piezoelectric speaker. A variety of suitable piezoelectric speakers are available, including from Murata Manufacturing Co., Ltd., with North American corporate headquarters in Smyrna, Ga. (see, e.g. the Murata catalog titled "Piezoelectric Sounds Components" labeled P37E and dated Jan. 28, 2010, which is incorporated herein by reference). Some embodiments can include acoustic transmission units such as those manufactured by Advanced Telemetry Systems (headquartered in Isanti, Minn.) for the Pacific Northwest National Laboratory (see, e.g. JSATS Acoustic Transmitter information sheet from the Pacific Northwest National Laboratory, updated March 2010, which is incorporated herein by reference). In some embodiments, an appurtenance can include a piezoelectric speaker configured as part of an acoustic transmitter and also to act as a signaling device (e.g. to generate a beeping noise in response to a signal from the processor).

In some embodiments, the transmission unit can include an ultrasonic transmitter. In some embodiments, the transmission unit can include an ultrasonic transducer. Multiple examples of ultrasonic transmitters and transducers are commercially available, often marketed under the term "ultrasonic sensors" as it is used in the industry (see, e.g. the Murata catalog titled "Ultrasonic Sensor" labeled 515E and dated Oct. 31, 2008, which is incorporated herein by reference). The transmission unit can be configured as part of an ultrasonic ranging system. See: Wang, "A Design Method of Ultrasonic Ranging System with High Accuracy," *Journal of Computational Information Systems*, 7: 7 pages 2444-2451 (2011), which is incorporated herein by reference. The transmission unit can be configured to communicate with an ultrasonic communication system. See: Chen and Wu, "Ultrasonic System with Infrared Communication Technology," *Journal of Computers*, vol. 6, no. 11, pages 2468-2475 (2011), which is incorporated herein by reference.

In some embodiments, the transmission unit can include an optical transmitter. For example, an optical transmission unit can include one or more white light emitting diodes (LEDs). For example, an optical transmission unit can include an infrared laser. In some embodiments, optical transmission units can be desirable to minimize interference from nearby electrical equipment, such as medical equipment. See: Kavehrad, "Sustainable Energy-Efficient Wireless Applications Using Light," *IEEE Communications Magazine*, vol. 48, no. 12, pages 66-73, (2010); and Fadlullah and Kavehrad, "Indoor High-Bandwidth Optical Wireless Links for Sensor Networks" *Journal of Lightwave Technology*, vol. 28, no. 21, pages 3086-3094 (2010), which are incorporated herein by reference.

Figure 3:
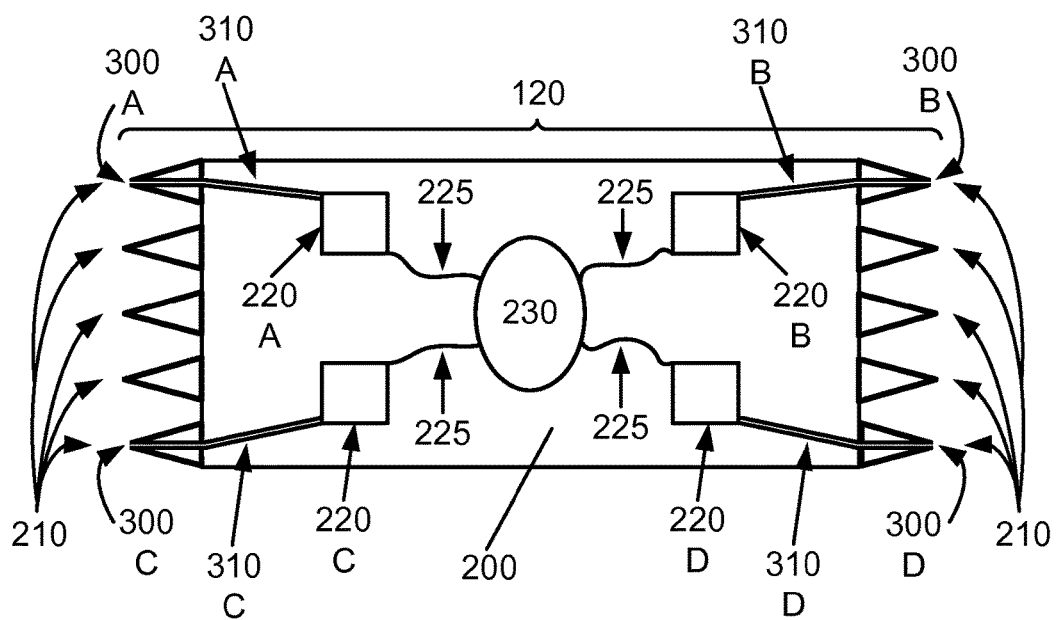
FIG. 3 is a schematic of an appurtenance to a wound dressing.

FIG. 3 illustrates aspects of an embodiment of an appurtenance to a wound dressing. The appurtenance 120 shown in FIG. 3 includes a substantially planar structure with a first set of a plurality of projections 210 attached to a first end of a substrate 200 (e.g. the left side as shown in FIG. 3) and a second set of a plurality of projections 210 attached to a second end of the substrate 200 (e.g. the right side as shown in FIG. 3). In the embodiment illustrated, each set of projections includes five projections. In the embodiment illustrated, some of the plurality of projections include substantially hollow structures including a proximal end affixed to an edge of the substrate, and a distal end including an aperture. In the embodiment illustrated, some of the plurality of projections of the appurtenance include a channel internal to at least one of the plurality of projections, the channel attached to a first aperture at a distal end of the projection, the channel attached to a second aperture positioned adjacent to the substrate, and an enclosed tubular structure attached to the substrate, the enclosed tubular structure affixed to the second aperture at a first end, the tubular structure affixed to a sensor unit at a second end. Some embodiments further include: one or more walls forming a gas-sealed chamber attached to the enclosed tubular structure, the gas-sealed chamber including an internal gas pressure below atmospheric pressure; and a breakable seal between the gas-sealed chamber and the enclosed tubular structure. Some embodiments include projections with an internal channel as well as projections without an internal channel. In some embodiments all of the projections include internal channels.

For example, FIG. 3 illustrates a projection at the upper left of the substrate including an interior hollow channel 300 A positioned along the main axis of the projection 210. The interior hollow channel 300 A has a distal end terminating at an aperture in the projection at a location substantially corresponding to the tip of the conical projection. The interior hollow channel 300 A has a proximal end affixed to the edge of the substrate 200. The proximal end of the hollow channel 300 A of the projection 210 is affixed to an enclosed tubular structure 310 A attached to the substrate 200. The enclosed tubular structure 310 A has a first end affixed to the hollow channel 300 A of the projection 210, and a second end attached to a sensor unit 220. Similarly, the appurtenance 120 illustrated in FIG. 3 includes projections 210 affixed to the substrate at positions adjacent to the corners of the substrate 200, each of which include a channel 300 A, 300 B, 300 C, 300D internal to at least one of the plurality of projections 210, the channel 300 A, 300 B, 300 C, 300D attached to a first aperture at a distal end of the projection 210, the channel 300 A, 300 B, 300 C, 300D attached to a second aperture positioned adjacent to the substrate 200. Each of the channels 300 A, 300 B, 300 C, 300D internal to a projection 210 is attached to an enclosed tubular structure 310 A, 310 B, 310 C, 310 D attached to the substrate 200.

Some embodiments include desiccant material within one or more of the channels 300 A, 300 B, 300 C, 300D internal to at least one of the plurality of projections 210. Some embodiments include desiccant material within an enclosed tubular structure 310 A, 310 B, 310 C, 310 D attached to the substrate 200. For example, a desiccant material can be selected and positioned to encourage fluid flow along the channel 300 A, 300 B, 300 C, 300D of a projection 210 or along an enclosed tubular structure 310 A, 310 B, 310 C, 310 D attached to the substrate 200. A desiccant material can be selected as suitable for a particular embodiment based on its cost, mass, or efficiency. For example, in some embodiments a desiccant material includes one or more of: activated charcoal, calcium sulfate, calcium chloride, or a zeolite. Some embodiments include sorbent material within one or more of the channels 300 A, 300 B, 300 C, 300D internal to at least one of the plurality of projections 210. Some embodiments include sorbent material within an enclosed tubular structure 310 A, 310 B, 310 C, 310 D attached to the substrate 200. For example, a sorbent material can be selected and positioned to encourage fluid flow along the channel 300 A, 300 B, 300 C, 300D of a projection 210 or along an enclosed tubular structure 310 A, 310 B, 310 C, 310 D attached to the substrate 200. A sorbent material can be selected as suitable for a particular embodiment based on its cost, mass, or efficiency of sorption of wound fluid. For example, in some embodiments a sorbent includes one or more of: a cellulose fiber, a polypropylene fiber, or a hydrophilic gel material.

Figure 4A:
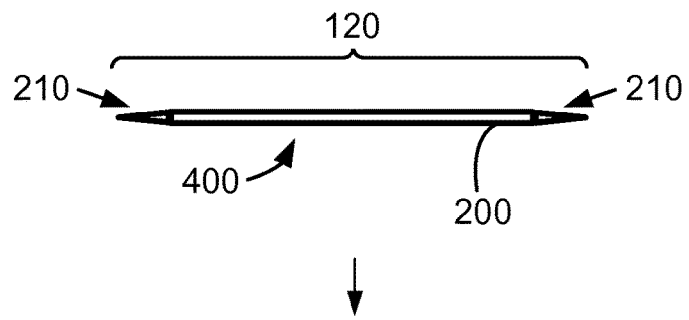
FIG. 4A is a schematic of an appurtenance to a wound dressing.
Figure 4A:

FIG. 4A illustrates an appurtenance 120 including a substrate 200 that is a substantially planar structure. The view of FIG. 4A shows the appurtenance in a side view (i.e. substantially at right angles to the view of FIG. 3). The substrate includes a surface 400 of a size and shape to mate with a surface of a wound dressing. Some embodiments include an appurtenance including at least one substantially planar surface of a size and shape to mate with a substantially planar surface of a wound dressing. Some embodiments include an appurtenance including at least one surface of a size and shape to mate with a surface of a wound dressing, wherein the surface of the wound dressing is a substantially non-planar surface. For example, the surface of a wound dressing may include one or more regularly spaced ridges, grooves, bumps or indentations and the surface of an appurtenance can include corresponding ridges, grooves, bumps or indentations as required to mate with the wound dressing surface. Some embodiments include a plurality of projections extending outward along a largest linear dimension of the substrate. For example FIG. 4A illustrates a substrate 200 at a side view along the longest axis (e.g. right to left in the illustration) and projections 210 with their longest axes substantially positioned along the same plane as the longest axis of the substrate 200.

Figure 4B:
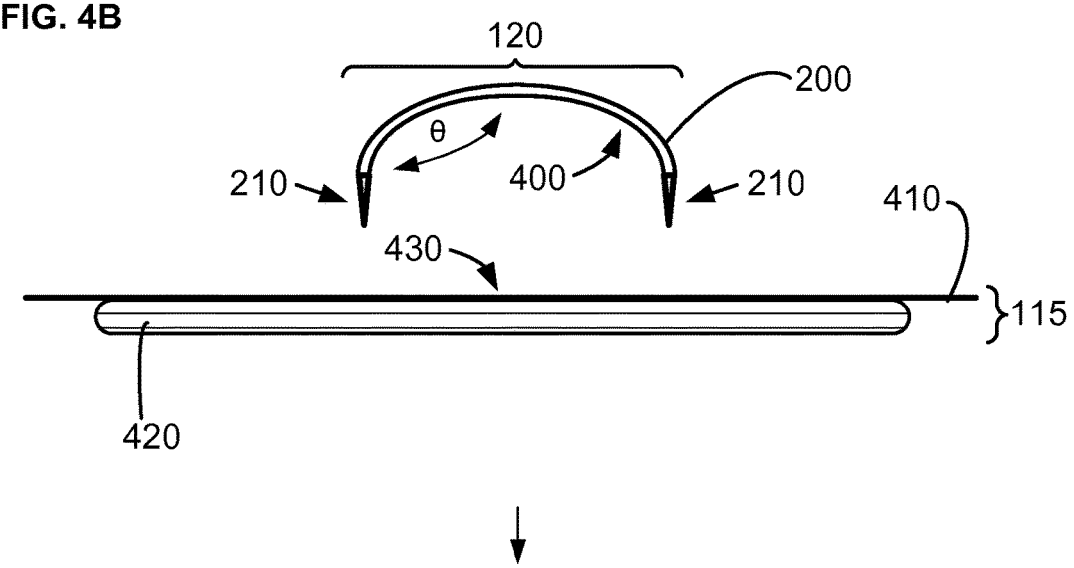
FIG. 4B is a schematic of an appurtenance adjacent to a wound dressing.
Figure 4C:
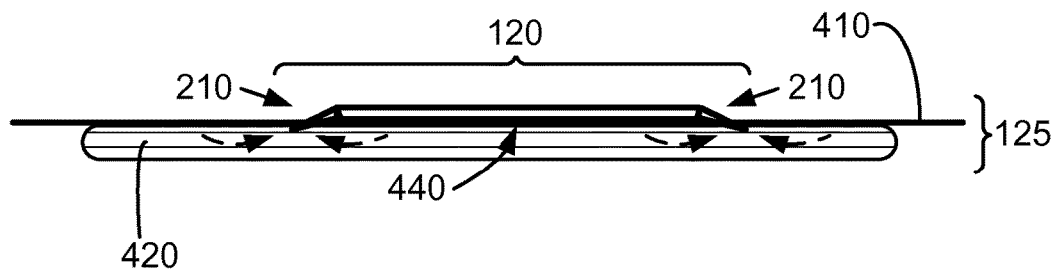
FIG. 4C is a schematic of an appurtenance attached to a wound dressing.

FIG. 4B depicts an appurtenance 120 including a substrate 200 and a wound dressing 115. The view of FIG. 4B is a side view, similar to the view of FIG. 4A. The wound dressing 115 illustrated includes dressing layer 420 and an outer layer 410. Not all wound dressings 115 should be expected to include multiple layers, and it is to be expected that some wound dressings 115 substantially include only a wound dressing material and not additional layers, structures or coverings. However, as illustrated in FIGS. 4B and 4C, in some embodiments wound dressings 115 include a plurality of layers. For example, a wound dressing 115 can include one or more outer layers configured to protect and isolate the wound dressing layer(s) from microbes, external dirt and debris, dryness, wetness or other external factors. An outer layer can be fabricated from materials such as firm plastics or mesh materials. An outer layer can include a surface larger than the surface of the wound dressing layer, and can include adhesives on that surface configured to adhere the entire wound dressing to a body surface. A wound dressing can include one or more layers of wound dressing materials, such as gauze, films, foams, or sponges. A wound dressing can include one or more layers of hydrogels, colloid gels, and medicinal agents impregnated within one or more layers of the wound dressing or on a surface of the wound dressing configured to face a wound.

The appurtenance 120 illustrated in FIG. 4B is a flexible structure along a long axis of the substrate 200. Although the illustrated embodiment is expected to generally be a flat or substantially planar structure in the absence of external force, in the view of FIG. 4B the appurtenance 120 has been flexed or bent in response to an external force (e.g. pressure from a person's fingers) so that each side of the appurtenance is bent by angle $\theta$ relative to a midline of the appurtenance. In some embodiments, an angle $\theta$ can be a range of degrees. For example, in some embodiments, an angle $\theta$ can be between approximately 20 and approximately 50 degrees. For example, in some embodiments, an angle $\theta$ can be approximately 20 degrees, approximately 25 degrees, approximately 30 degrees, approximately 35 degrees, approximately 40 degrees, approximately 45 degrees, or approximately 50 degrees. The appurtenance 120 is bent with surface 400 facing the interior angle to mate with a surface 430 of the wound dressing 115. In some embodiments, during application of an appurtenance to a wound dressing, a flexible appurtenance is bent by a user, after which time the sets of projections affixed to opposing ends of the substrate are placed adjacent to the exterior surface of the wound dressing. When the user releases the appurtenance, it then flexes back to a substantially planar structure, with the sets of projections extending into the interior of the wound dressing (see, e.g. FIG. 4C). In some embodiments, the substrate is flexible and each of the plurality of projections include a proximal end and a distal end, with the projections tapering in size from the proximal end to the distal end. The distal end of the projections are positioned at the surface of the wound dressing while the appurtenance is bent, such that when the appurtenance is released it flexes back to a planar shape and the projections are forced into the surface of the wound dressing.

FIG. 4C illustrates an appurtenance 120 similar to those shown in FIGS. 4A and 4B, with the appurtenance affixed to a wound dressing to create an appurtenance affixed to a wound dressing combination unit, 125. Surfaces of the appurtenance 120 and the outer layer 410 are mated at a junction 440 interior to the appurtenance affixed to a wound dressing combination unit, 125. The sets of projections 210 affixed to the ends of the appurtenance 120 include distal ends that are embedded in the wound dressing. The ends of the projections 210 traverse the outer layer 410 of the wound dressing into the dressing layer 420. During use, fluid in the dressing can flow into the ends of the projections 210 that include an internal channel, as shown by the dotted lines in FIG. 4C.

Figure 5A:
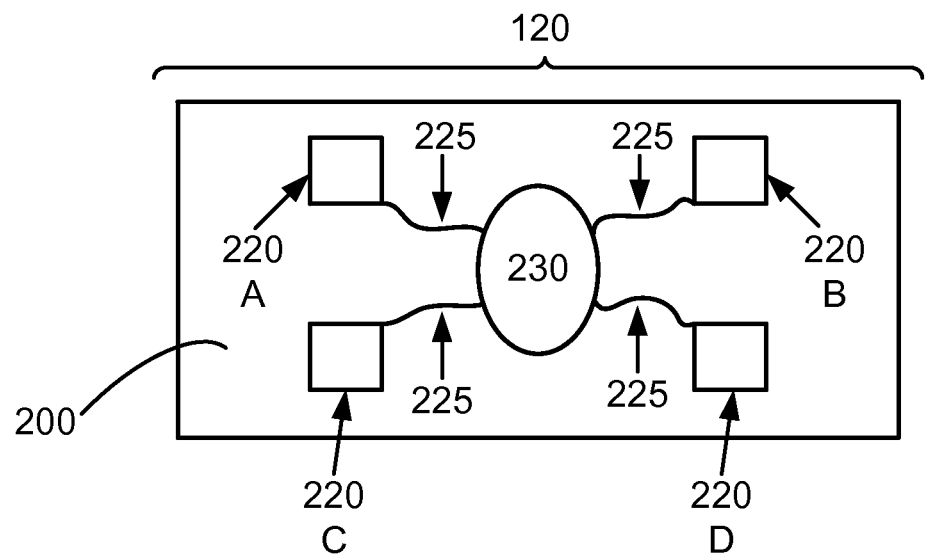
FIG. 5A is a schematic of an appurtenance to a wound dressing.

FIG. 5A shows aspects of an embodiment of an appurtenance 120 to a wound dressing. The appurtenance 120 includes a substrate 200 that is a substantially planar structure shown in a "top-down" viewpoint. A plurality of sensor units 220 are affixed to the substrate 200 at regular intervals. Wire connectors 225 connect each of the plurality of sensor units 220 to a transmission unit 230.

Figure 5B:
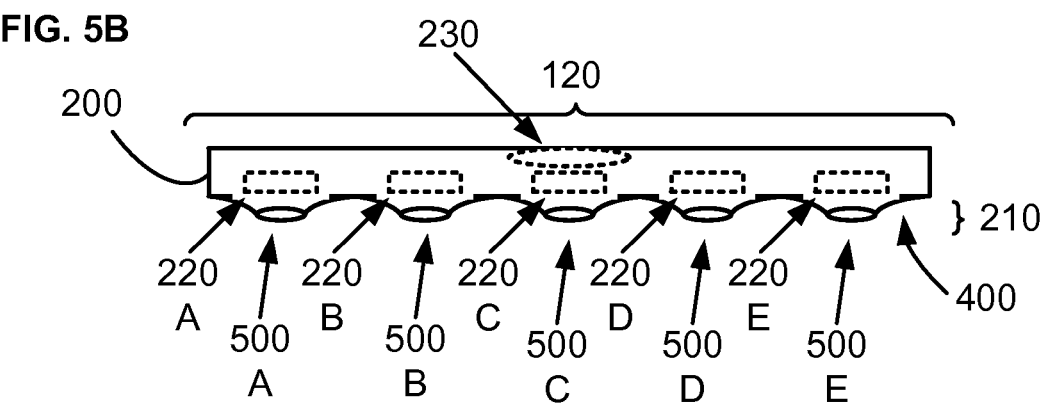
FIG. 5B is a schematic of an appurtenance to a wound dressing.

FIG. 5B shows aspects of an appurtenance 120 with a substrate 200 that is a substantially planar structure, shown in a side viewpoint. For purposes of illustration, some internal structures of the appurtenance 120 are depicted with dotted lines to show relative position and orientation of the components of the appurtenance 120. The appurtenance 120 includes a plurality of projections 220 affixed to the surface 400 of the appurtenance 120 that is of a size and shape to mate with a surface of a wound dressing. In some embodiments, the plurality of projections are each sized and positioned to mate with a non-planar surface of a wound dressing, for example a surface with channels, grooves, divots or indentations. In the illustrated embodiment, each of the plurality of projections 220 is a substantially hollow structure. In the illustrated embodiment, each of the plurality of projections 220 is a substantially conical structure. In the illustrated embodiment, each of the plurality of projections 220 includes an aperture 500 adjacent to the surface 400. Internal to the appurtenance 120 there are a plurality of sensor units 220, with each sensor unit 220 positioned adjacent to an aperture 500. Some embodiments include a plurality of sensor units wherein each sensor unit is positioned in direct contact with an aperture in a projection. Some embodiments include a plurality of sensor units wherein each sensor unit is positioned in indirect contact with an aperture in a projection, such as including a gap between the aperture and the sensor unit, and including sorbent material within the gap. In the embodiment shown in FIG. 5B, each of the plurality of sensor units 220 are connected to a transmission unit 230 positioned within the structure of the appurtenance 120. For example, in some embodiments an appurtenance includes wire connectors.

Figure 6A:
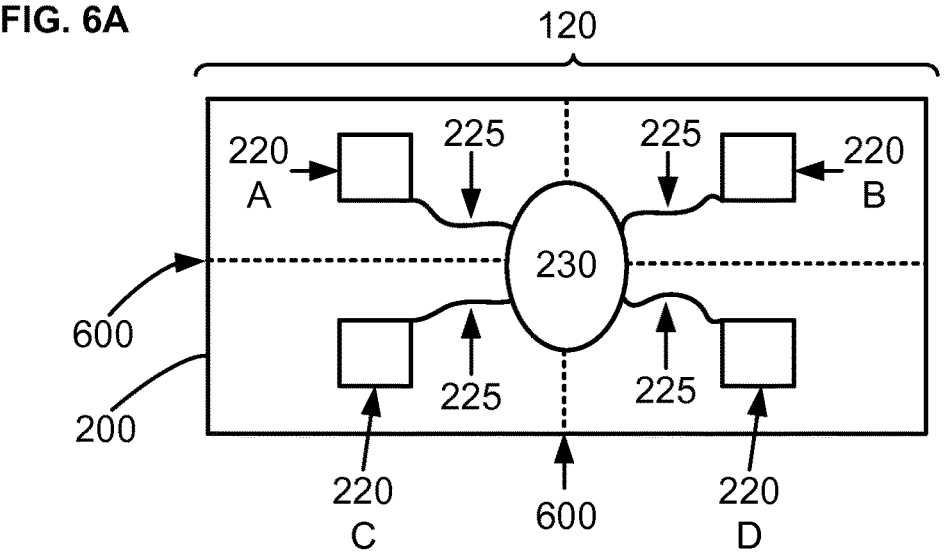
FIG. 6A is a schematic of an appurtenance to a wound dressing.

FIG. 6A shows aspects of an embodiment of an appurtenance 120 to a wound dressing. The appurtenance 120 includes a substrate 200 that is a substantially planar structure shown in a "top-down" viewpoint. A divider 600 is positioned to separate the substantially rectangular and planar substrate into four quadrants. A plurality of sensor units 220 are affixed to the substrate 200, with one sensor unit positioned substantially within each of the quadrants.

The divider 600 in the embodiment illustrated in FIG. 6A is positioned to partition the interior of the substrate 200 structure so that the plurality of sensor units 220 are each separated from each other by the divider 600. In some embodiments, a divider is positioned within the substrate structure in a location that separates the interior of the substrate into a series of regularly-sized compartments. In some embodiments, a divider is positioned within the substrate structure in a location that separates the interior of the substrate into a series of irregularly-sized compartments. In some embodiments, there is at least one flexible divider internal to the substrate, the flexible divider positioned between a first sensor unit and a second sensor unit. A flexible divider, for example, can be fabricated with sufficient strength to maintain its position and integrity even when the entire substrate structure is bent or flexed (e.g. see FIG. 4B). Wire connectors 225 connect each of the plurality of sensor units 220 to a transmission unit 230.

A "divider" to an appurtenance, as discussed herein, is an internal structure positioned within the substrate. For example, in embodiments including a substrate with at least two walls, a divider can be positioned between the walls, with a first edge of the divider affixed to a first wall and a second edge of the divider attached to a second wall of the substrate. In embodiments including a substrate with at least two walls and sorbent or desiccant material positioned between the walls, a divider is positioned to separate a first section of sorbent or desiccant material and a second section of sorbent or desiccant material. In embodiments wherein a substrate is a foam structure, a divider can include a structure within the foam that partitions one section of the foam from an adjacent section. A divider can be fabricated, for example, from a thin plastic material, such as a thin plastic sheet. A divider can be fabricated, for example, from a thin polyester material, such as a thin PET sheet. A divider can be fabricated, for example, from a thermally reflective material, such as a metalized boPET sheet. In some embodiments, a divider is fabricated from the same material as the associated substrate. A divider is positioned to internally separate sections of the substrate, for example to minimize wound fluid wicking through the interior of the substrate. A divider material, depending on the embodiment, is selected to be non-porous to wound fluid within the substrate structure. A divider material, depending on the embodiment, is selected to be thermally reflective.

Figure 6B:
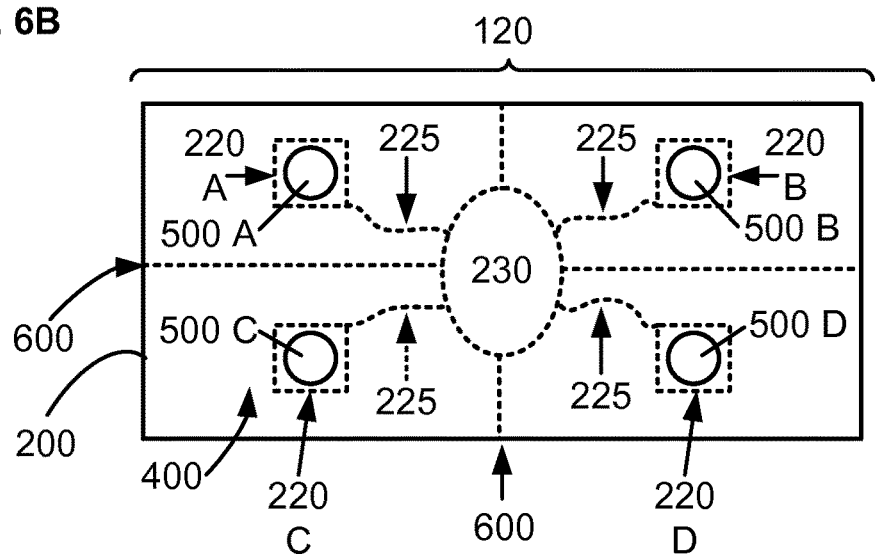
FIG. 6B is a schematic of an appurtenance to a wound dressing.

FIG. 6B illustrates aspects of an appurtenance 120. The view shown in FIG. 6B is a substantially "bottom up" view of the appurtenance, so that the surface 400 configured to mate with the surface of a wound dressing is visible. For purposes of illustration, internal structures are shown with dotted lines. The substrate 200 has four projections (see, e.g. as shown in FIG. 5B) at the surface 400 configured to mate with the surface of a wound dressing. Each of the four projections 500 is positioned in a quadrant of the substrate, with an internal divider 600 separating the internal substrate 200 quadrants. The substrate 200 includes four projections, each of which terminate with an aperture 500. A sensor unit 220 is positioned adjacent to each aperture 500. Each sensor unit 220 is connected to a centrally-positioned transmission unit 230 with a wire connector 225.

Figure 6C:
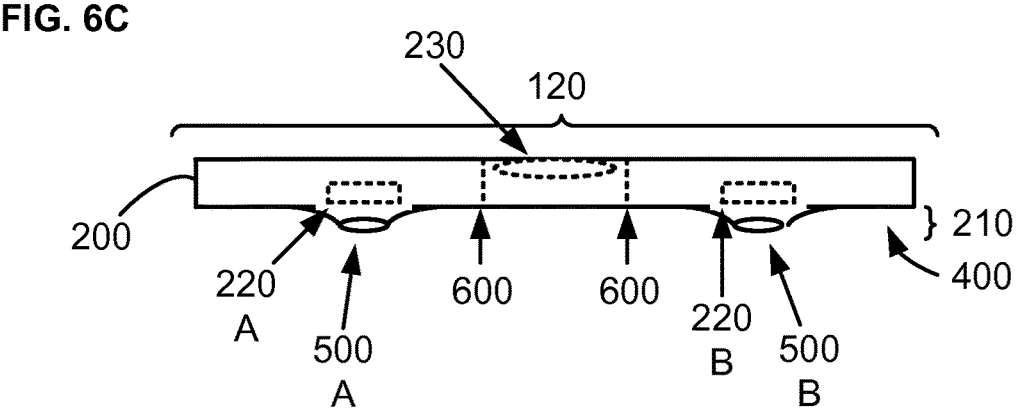
FIG. 6C is a schematic of an appurtenance to a wound dressing.

FIG. 6C illustrates aspects of an embodiment of an appurtenance 120. The appurtenance 120 shown in FIG. 6C is a substantially planar appurtenance, shown at an edge view with some interior structures depicted with dotted lines for purposes of illustration. The embodiment includes a substrate 200 with walls surrounding an interior space. A divider 600 is positioned within the interior space, the divider including a first end attached to a first wall and a second end attached to a second wall. A transmission unit 230 is centrally positioned within the interior space. The substrate includes projections 210 positioned on the surface 400 configured to mate with a surface of a wound dressing. Each of the projections 210 ends with a distal aperture 500. A sensor unit 220 is positioned within the interior of the substrate 200, each sensor unit 220 positioned adjacent to an aperture 500 and separated from the adjacent sensor unit(s) 220 by the divider 600. For example, sensor unit 220 A and sensor unit 220 B shown in FIG. 6C are partitioned from each other with a central divider 600.

Figure 7:
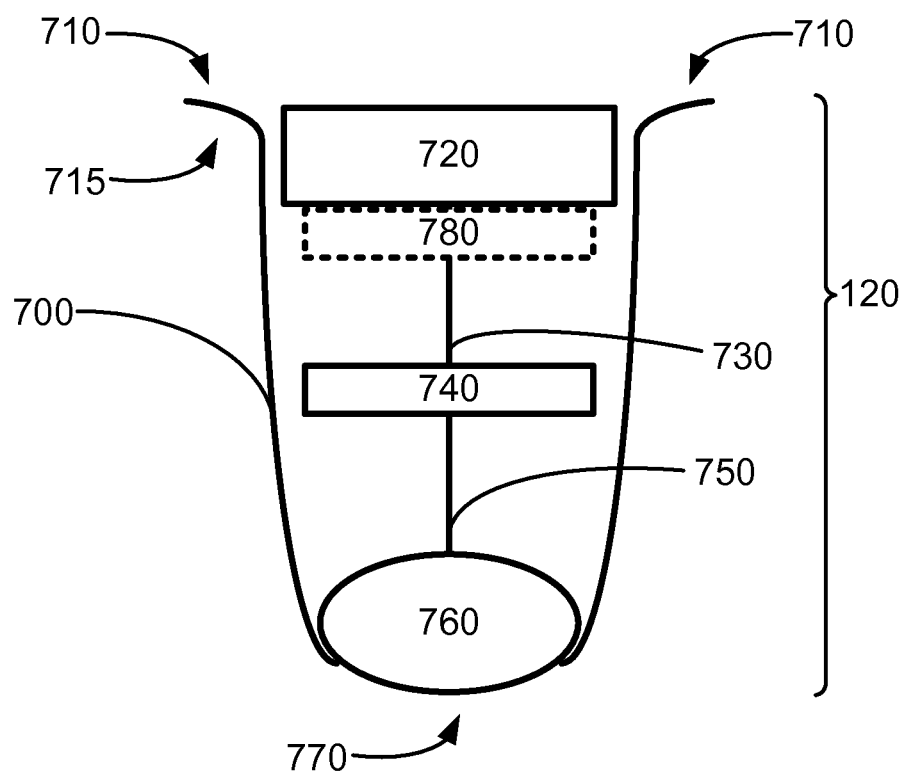
FIG. 7 is a schematic of an appurtenance to a wound dressing.

Some embodiments include an appurtenance to a wound dressing, including: an enclosure including at least one external surface of a size and shape to mate with a surface of a wound dressing; one or more sensor units affixed to the enclosure, the one or more sensor units configured to sense a condition of the wound dressing; a processor operably coupled to the one or more sensor units; and at least one transmission unit operably coupled to the processor, the transmission unit including circuitry configured to transmit information associated with the one or more sensor units. For example, FIG. 7 illustrates an appurtenance 120 including an enclosure 700. The view shown in FIG. 7 includes a substantially cross-section view of an appurtenance 120 to illustrate internal features of the appurtenance. The enclosure 700 substantially defines the exterior surface of the appurtenance 120. The enclosure 700 includes a flange 710 positioned at an edge of the enclosure. In some embodiments, a flange 710 includes a surface 715 positioned to contact a surface of a wound dressing when the appurtenance 120 is in use with a wound dressing. An aperture 770 is positioned within the enclosure 700. Some embodiments include a single aperture in the enclosure. For example, some embodiments include a single aperture at an end region of the appurtenance. Some embodiments include a plurality of apertures in the enclosure. For example, some embodiments include a plurality of apertures positioned at regular intervals around the surface of the enclosure.

Some embodiments include an appurtenance wherein the enclosure is a substantially cylindrical structure. Some embodiments include an appurtenance wherein the enclosure is a substantially conical structure. Some embodiments include an appurtenance wherein the enclosure is a substantially elliptical structure. Some embodiments include an appurtenance wherein the at least one external surface of a size and shape to mate with a surface of a wound dressing is substantially smooth. Some embodiments include an appurtenance wherein the enclosure includes at least one external surface of a size and shape to mate with the surface of an aperture within the wound dressing. Some embodiments include an appurtenance wherein the enclosure includes at least one external surface of a size and shape to mate with the surface of the wound dressing, wherein the surface is a curved surface. Some embodiments include an appurtenance wherein the enclosure includes at least one external surface of a size and shape to mate with the surface of the wound dressing, wherein the surface is a flexed surface. Some embodiments include an appurtenance wherein the enclosure includes at least one external surface of a size and shape to mate with the surface of the wound dressing, wherein the surface is a substantially non-planar surface. Some embodiments include an appurtenance wherein the enclosure includes at least one external surface including at least one chemical adherent positioned to affix the wound dressing to the enclosure. Some embodiments include an appurtenance wherein the enclosure is of a height and width to fit substantially through an aperture in the wound dressing, the enclosure including at least one surface configured to mate with a surface of the aperture within an interior region of the wound dressing. Some embodiments include an appurtenance wherein the enclosure includes one or more protuberances affixed to the at least one external surface. Some embodiments include an appurtenance wherein the enclosure includes one or more indentations in the at least one external surface. Some embodiments include an appurtenance wherein the enclosure includes one or more apertures in the at least one external surface. Some embodiments include an appurtenance wherein the enclosure includes a desiccant material within the enclosure. Some embodiments include an appurtenance wherein the enclosure includes a desiccant material positioned entirely within the enclosure, and the desiccant material is in fluid communication with the wound dressing.

An enclosure for an appurtenance can be fabricated from a variety of materials, depending on the embodiment. For example, in some embodiments an enclosure of an appurtenance is fabricated from a plastic material. For example, in some embodiments an enclosure of an appurtenance is fabricated from a metal. For example, in some embodiments an enclosure of an appurtenance is fabricated from a paper-based material of sufficient toughness for the required durability of an embodiment. Some embodiments include a fluid transport film affixed to the enclosure. For example, some embodiments include a fluid transport film affixed to an interior surface of the enclosure. For example, some embodiments include a fluid transport film affixed to an interior surface of the enclosure adjacent to one or more apertures, with the fluid transport film positioned to direct fluid into the interior of the enclosure through at least one aperture. Some embodiments include a fluid control film affixed to the enclosure. For example, some embodiments include a fluid control film affixed to an interior surface of the enclosure. For example, some embodiments include a fluid control film affixed to an interior surface of the enclosure through the interior surface, with apertures in the fluid control film corresponding to apertures in the enclosure of the appurtenance. For example, some embodiments include a fluid control film affixed to an interior surface of the enclosure adjacent to one or more sensor units, with the fluid control film positioned to isolate a surface of the one or more sensor units from a flow of wound fluid internal to the appurtenance.

FIG. 7 illustrates an embodiment with a sensor unit 760 positioned adjacent to the single aperture 770 in the enclosure. The sensor unit 760 is positioned and angled to detect properties of the wound dressing and/or wound fluid in the wound dressing. For example, the sensor unit can, in some embodiments, be positioned and/or angled to detect properties including at least one of: temperature, fluid pressure, moisture, or the presence of one or more specific proteins (e.g. MMPs). In some embodiments, a sensor unit includes a chemical sensor. In some embodiments, a sensor unit includes a resonance sensor. In some embodiments, a sensor unit includes at least one antibody. In some embodiments, a sensor unit includes at least one aptimer. In some embodiments, a sensor unit includes a temperature sensor. In some embodiments, a sensor unit includes a plurality of sensors within each sensor unit. In some embodiments, a sensor unit includes: a sensor; circuitry for accepting data from the sensor; and circuitry for sending the accepted data to the processor. In some embodiments, a sensor unit includes: reversible fasteners of a size and shape for attachment to the substrate.

Some embodiments include: an aperture in the enclosure; a channel including a first end affixed to the enclosure and a second end affixed to the sensor unit; one or more walls forming a gas-sealed chamber adjacent to the channel, the gas-sealed chamber with an internal gas pressure below atmospheric pressure; an aperture in the one or more walls of the gas-sealed chamber at a position adjacent to the channel; a breakable seal at the aperture in the one or more walls of the gas-sealed chamber; an aperture in the channel at a position corresponding to the aperture in the one or more walls of the gas-sealed chamber; and a seal between the aperture in the one or more walls of the gas-sealed chamber and the aperture in the channel. Some embodiments include at least one desiccant material. Some embodiments include at least one desiccant material in fluid communication with the interior of the wound dressing. Some embodiments include at least one sorbent material. Some embodiments include at least one sorbent material in fluid communication with the interior of the wound dressing.

FIG. 7 illustrates an embodiment including a processor 740. The processor 740 is positioned within the enclosure and is connected to the sensor unit 760 with a wire connector 750. In some embodiments, a processor includes: circuitry configured to accept data from at least one of the one or more sensor units; circuitry configured to process the accepted data; and circuitry configured to send the processed data to the at least one transmission unit. The embodiment shown in FIG. 7 includes a transmission unit 720. The transmission unit 720 is connected to the processor 740 with a wire connector. Some embodiments include a battery unit 780 operably connected to the processor. Some embodiments include a battery unit 780 operably connected to the transmission unit 720. For example, in some embodiments the transmission unit requires electrical power for full operation, which is supplied from an associated battery.

Figure 8:
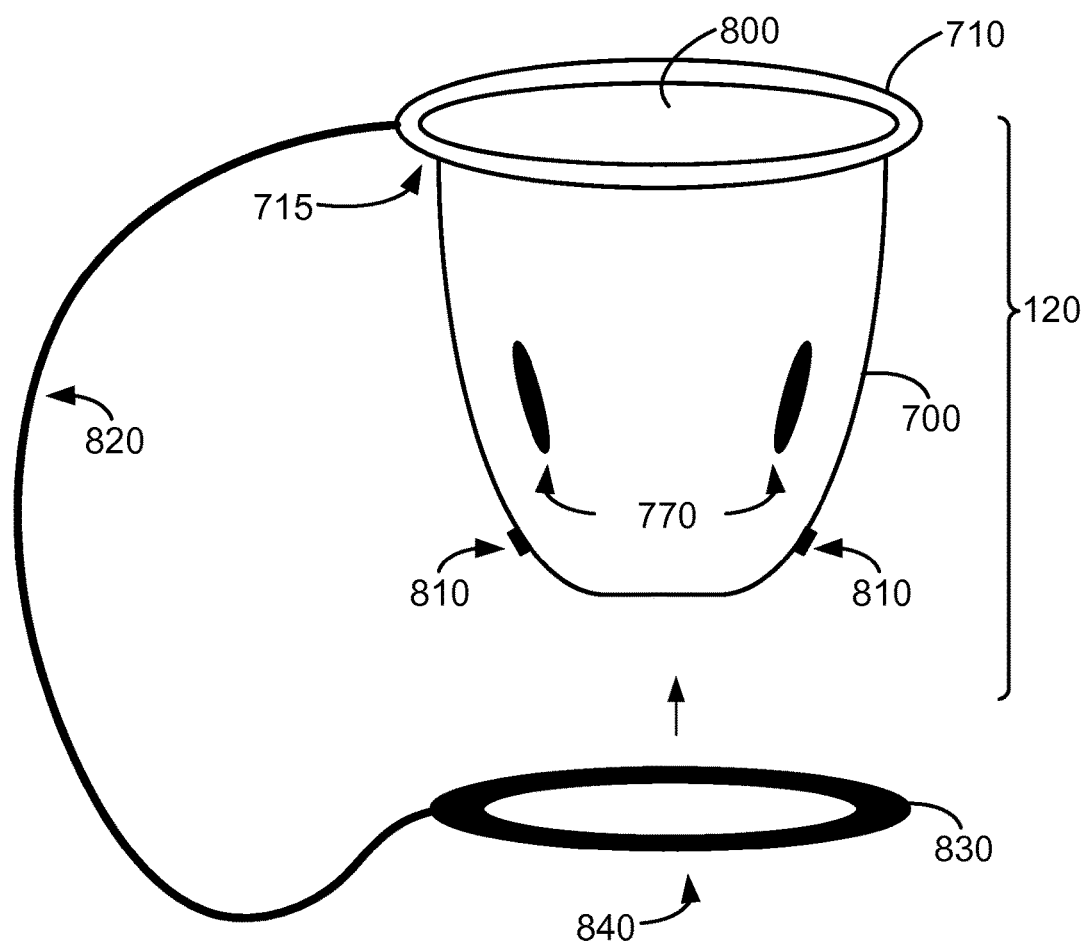
FIG. 8 is a schematic of an appurtenance to a wound dressing.

FIG. 8 illustrates an embodiment of an appurtenance to a wound dressing. The appurtenance 120 illustrated in FIG. 8 is depicted as an exterior view, with the interior features (e.g. as shown in FIG. 7) not visible in FIG. 8. The appurtenance 120 includes an enclosure, which includes a flange 710 with a surface 715 positioned to contact a surface of a wound dressing when the appurtenance 120 is in use with a wound dressing. A top surface 800 of the appurtenance is a substantially planar surface positioned to be substantially parallel with the plane of the wound dressing when the appurtenance 120 is in use with a wound dressing. Two apertures 770 in the enclosure 700 are visible in the view of FIG. 8. Some embodiments include an appurtenance with one or more protuberances affixed to the external surface of the enclosure. For example, the embodiment shown in FIG. 8 includes an enclosure 700 with two protuberances 810 affixed to the exterior surface. Some embodiments include one or more protuberances that are shaped as a ring or groove around a circumference of a circular enclosure. Some embodiments include an indentation in the exterior of the enclosure. For example, a protuberance can be fabricated from the same material as the enclosure and be integral with the enclosure. For example, a protuberance can be affixed to the exterior surface of the enclosure after manufacture.

Some embodiments include: a tether with a first end affixed to the enclosure; and a securing unit affixed to a second end of the tether, the securing unit including a surface of a size and shape to mate with the external surface of the enclosure. Some embodiments include: one or more protuberances affixed to the external surface of the enclosure; and a securing unit including a surface of a size and shape to mate with the external surface of the enclosure including at least one of the one or more protuberances. Some embodiments include: one or more indentations in the external surface of the enclosure; and a securing unit including a surface of a size and shape to mate with the external surface of the enclosure including at least one of the one or more indentations. In some embodiments, an appurtenance includes a securing unit that is a closure unit. In some embodiments, an appurtenance includes a securing unit that is configured as a socket or a stud. In some embodiments, an appurtenance includes a region that is configured as a capped prong region, an open prong region, a capped post, and/or a post.

FIG. 8 illustrates an embodiment of an appurtenance including a tether 820 affixed to a securing unit 830. For example, in some embodiments a tether is fabricated from one or more of: pliable plastic, cotton twine, rubber or similar materials. The securing unit 830 includes an aperture 840 of a size and shape to mate with the exterior surface of the enclosure 700 and the two protuberances 810 affixed to the exterior surface. The securing unit can be, for example, fabricated from a plastic material, a ceramic material, a metal or a firm paper fiber material. In some embodiments, a securing unit is fabricated from the same material as the enclosure.

Figure 9A:
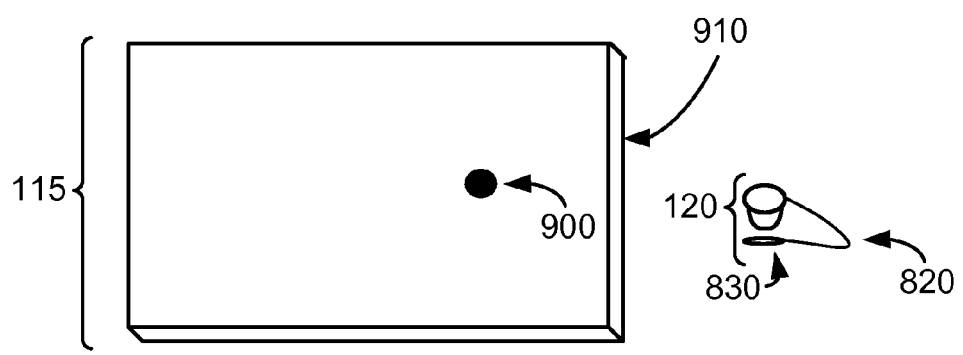
FIG. 9A is a schematic of an appurtenance and a wound dressing.

FIG. 9A depicts aspects of an appurtenance in use with a wound dressing. The appurtenance is configured for use with a subset of wound dressings of a predetermined approximate thickness and appropriately sized and shaped aperture. The appurtenance 120 includes an enclosure that is a substantially conical structure with a flat surface at the top, a tether 820 and a securing unit 830 affixed to the tether. The appurtenance 120 is fabricated with a size and shape for use with a substantially planar wound dressing 115 with a thickness 910 similar to the height of the enclosure of the appurtenance 120. The wound dressing 115 includes an aperture 900 with an interior surface of a size and shape to mate with the exterior surface of the enclosure of the appurtenance 120. The aperture 900 in the wound dressing can be positioned at a location of particular interest in wound monitoring, for example adjacent to a wound cavity. The aperture 900 in the wound dressing can be positioned at a location expected to result in minimal discomfort to the patient, for example at a position distal to a wound surface.

Figure 9B:
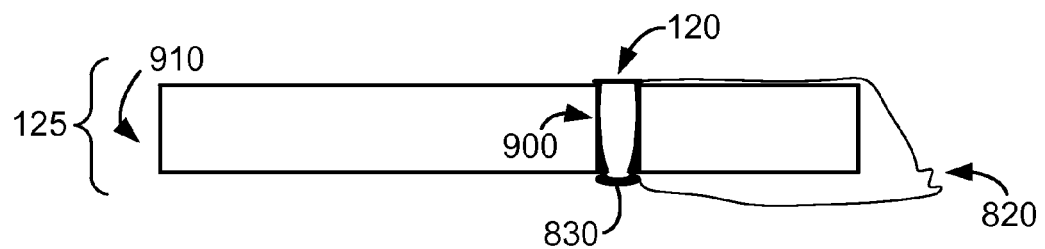
FIG. 9B is a schematic of an appurtenance attached to a wound dressing.

FIG. 9B illustrates an appurtenance and wound dressing similar to those shown in FIG. 9A, positioned as an appurtenance-wound dressing combination unit 125. The appurtenance 120 is positioned within the aperture 900 in the wound dressing, and has a long axis that is a similar dimension to the thickness 910 of the wound dressing. The securing unit 830 is affixed to the exterior of the appurtenance at a distal end of the appurtenance 120. The tether 820 wraps around the end of the wound dressing.

Figure 10A:
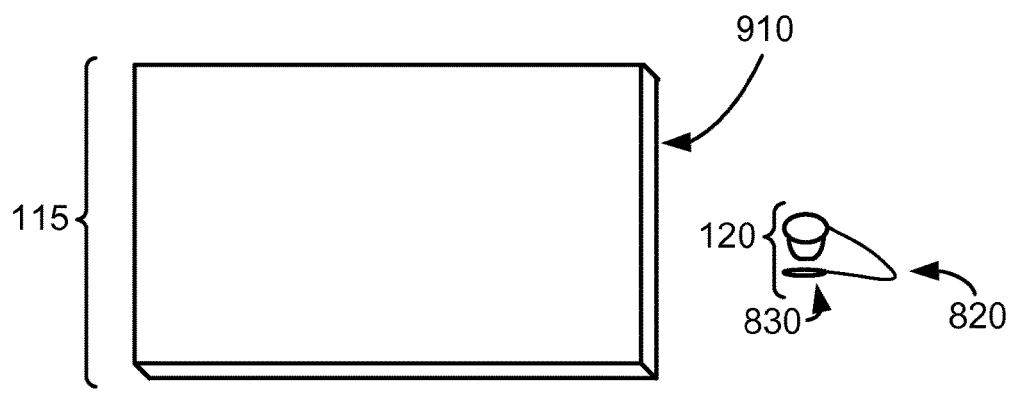
FIG. 10A is a schematic of an appurtenance and a wound dressing.

FIG. 10A depicts aspects of an appurtenance in use with a wound dressing. The appurtenance is configured for use with a subset of wound dressings of a predetermined approximate thickness and flexibility. For example, some embodiments of appurtenances are configured for use with a foam dressing. For example, some embodiments of appurtenances are configured for use with a flexible gauze dressing. The appurtenance 120 includes an enclosure that is a substantially conical structure with a flat surface at the top, a tether 820 and a securing unit 830 affixed to the tether. The appurtenance 120 is fabricated with a size and shape for use with a substantially planar wound dressing 115 with a thickness 910 similar to the height of the enclosure of the appurtenance 120.

Figure 10B:
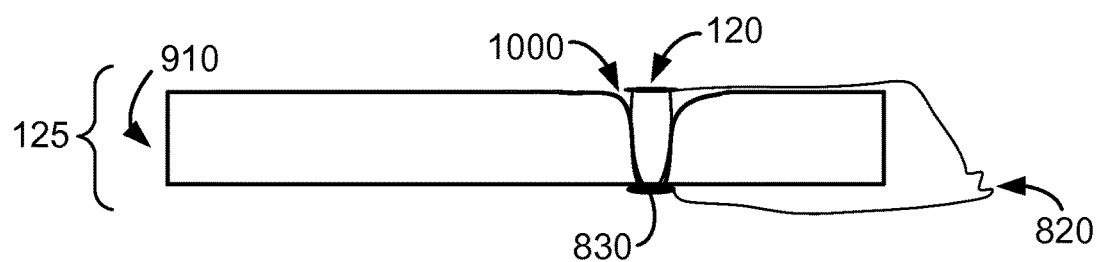
FIG. 10B is a schematic of an appurtenance attached to a wound dressing.

FIG. 10B illustrates an appurtenance and wound dressing similar to those shown in FIG. 10A, positioned as an appurtenance-wound dressing combination unit 125. The appurtenance 120 has a long axis that is a similar dimension to the thickness 910 of the wound dressing. The appurtenance 120 has been placed against a surface of the wound dressing, and then the structure of the wound dressing has been bent, flexed, and/or compressed to create a surface configuration 1000 that approximates the exterior of the appurtenance 120. A securing unit 830 is affixed to the appurtenance 120 at a distal end, which holds the surface configuration 1000 of the wound dressing in a stable state. The securing unit 830 is affixed to the exterior of the appurtenance at a distal end of the appurtenance 120. The tether 820 wraps around the end of the wound dressing. As desired by a caregiver, an appurtenance can be positioned at a location of a wound dressing particular interest for wound monitoring, for example adjacent to a wound cavity. As desired by a caregiver, an appurtenance can be positioned at a location of a wound dressing expected to result in minimal discomfort to the patient, for example at a position distal to a wound surface.

In some embodiments, an appurtenance to a wound dressing includes: an enclosure including an external surface, the external surface including a first portion of a size and shape to mate with an aperture in a wound dressing, the external surface including a second portion including a surface facing away from an exterior of the wound dressing; a flange attached to the external surface of the enclosure on or proximal to the second portion, the flange including a surface configured to mate with an outward-facing surface of the wound dressing; an end cap attached to the external surface of the enclosure; one or more sensor units affixed to the enclosure, the one or more sensor units including circuitry configured to sense a condition of a wound dressing environment; a processor operably coupled to the one or more sensor units; and at least one transmission unit operably coupled to the processor and operably coupled to the one or more sensor units, the transmission unit including circuitry configured to transmit information associated with the one or more sensor units.

Figure 11:
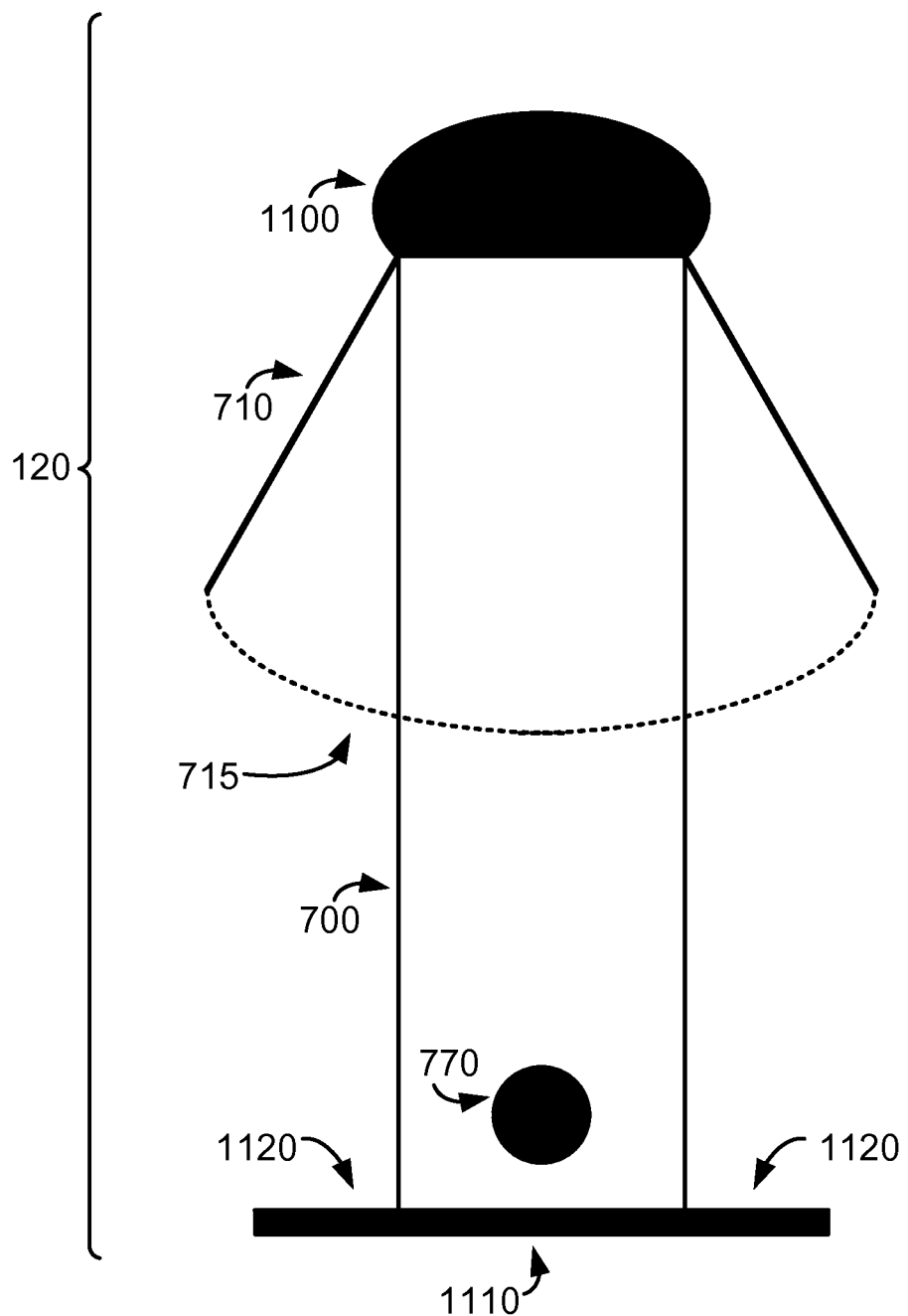
FIG. 11 is a schematic of an appurtenance to a wound dressing.

FIG. 11 illustrates aspects of an embodiment of an appurtenance 120. The appurtenance 120 is illustrated in an external side view. The appurtenance 120 includes an enclosure 700 that is a substantially cylindrical structure. In some embodiments, an enclosure is a substantially conical structure. In some embodiments, an enclosure is a substantially elliptical structure. The enclosure 700 includes an external surface of a size and shape to mate with a surface of a wound dressing. The external surface of a size and shape to mate with a surface of a wound dressing is substantially smooth. The enclosure 700 is of a height and width to fit substantially through an aperture in a wound dressing of a particular type (e.g. size and style). The enclosure 700 includes at least one surface configured to mate with a surface of the aperture within an interior region of the wound dressing. In some embodiments, an enclosure includes one or more apertures in the external surface. In the view shown in FIG. 11, the enclosure 700 includes one aperture 770.

The appurtenance 120 includes a flange 710 attached to a circumference of the external surface of the enclosure near a first end of the enclosure (e.g. the top in the view of FIG. 11). The flange includes a surface 715 configured to mate with an outward-facing surface of the wound dressing. The flange 710 is a planar structure affixed to the exterior surface of the enclosure at a top edge of the enclosure structure. The view of FIG. 11 depicts the flange 710 structure as transparent for illustration purposes. In some embodiments, a flange is flexible. In some embodiments, a flange is fabricated from a flexible material, such as a flexible rubber or a flexible plastic material. In some embodiments, a flange is fabricated from a material with sufficient flexibility so that the surface 715 of the flange 710 can reversibly move between a position essentially adjacent to the exterior surface of the enclosure 700 to a position essentially at right angles to the exterior surface of the enclosure 700 without damage to the flange 710. Some embodiments include at least one sensor unit affixed to a surface of the flange adjacent to an expected position of the wound dressing (e.g. surface 715 in FIG. 11). Some embodiments include a positioning element 1100 affixed to an end of the enclosure. For example, a positioning element can be of a size and shape to assist a user of the appurtenance to position the appurtenance relative to a wound dressing during use.

Some embodiments of an appurtenance include an end cap attached to the external surface of the enclosure at an end of the enclosure. For example, FIG. 11 illustrates an appurtenance 120 including an end cap 1110 attached to the external surface of the enclosure 700 at a second end of the enclosure 700. Some embodiments include an end cap attached to a surface of the enclosure adjacent to an end distal to the attachment site of a flange. In the embodiment shown in FIG. 11, the end cap 1110 is a substantially planar structure, affixed to the external surface of the enclosure 700 substantially perpendicularly to a long axis of the enclosure 700. In some embodiments, an end cap is substantially a disk structure. For example, the enclosure can be attached to the center region of an end cap that is a disk or disk-like structure. Depending on the embodiment, an end cap can be fabricated from the same material as the enclosure and fabricated as an integral structure with the enclosure. In some embodiments, an end cap is fabricated from a stiff material, such as a solid plastic or ceramic material. Some embodiments include a surface adjacent to an expected position of the wound dressing. For example, the embodiment of FIG. 11 includes a surface 1120 adjacent to an expected position of the wound dressing. The surface 1120 shown in FIG. 11 is a substantially planar surface of a size and shape to conform with a planar surface of a wound dressing. In some embodiments, a surface of an end cap adjacent to an expected position of a wound dressing includes one or more ridges, bumps, grooves or other structural features positioned to mate with a surface of a wound dressing. Some embodiments include at least one sensor unit affixed to a surface of the end cap adjacent to an expected position of the wound dressing.

Figure 12:
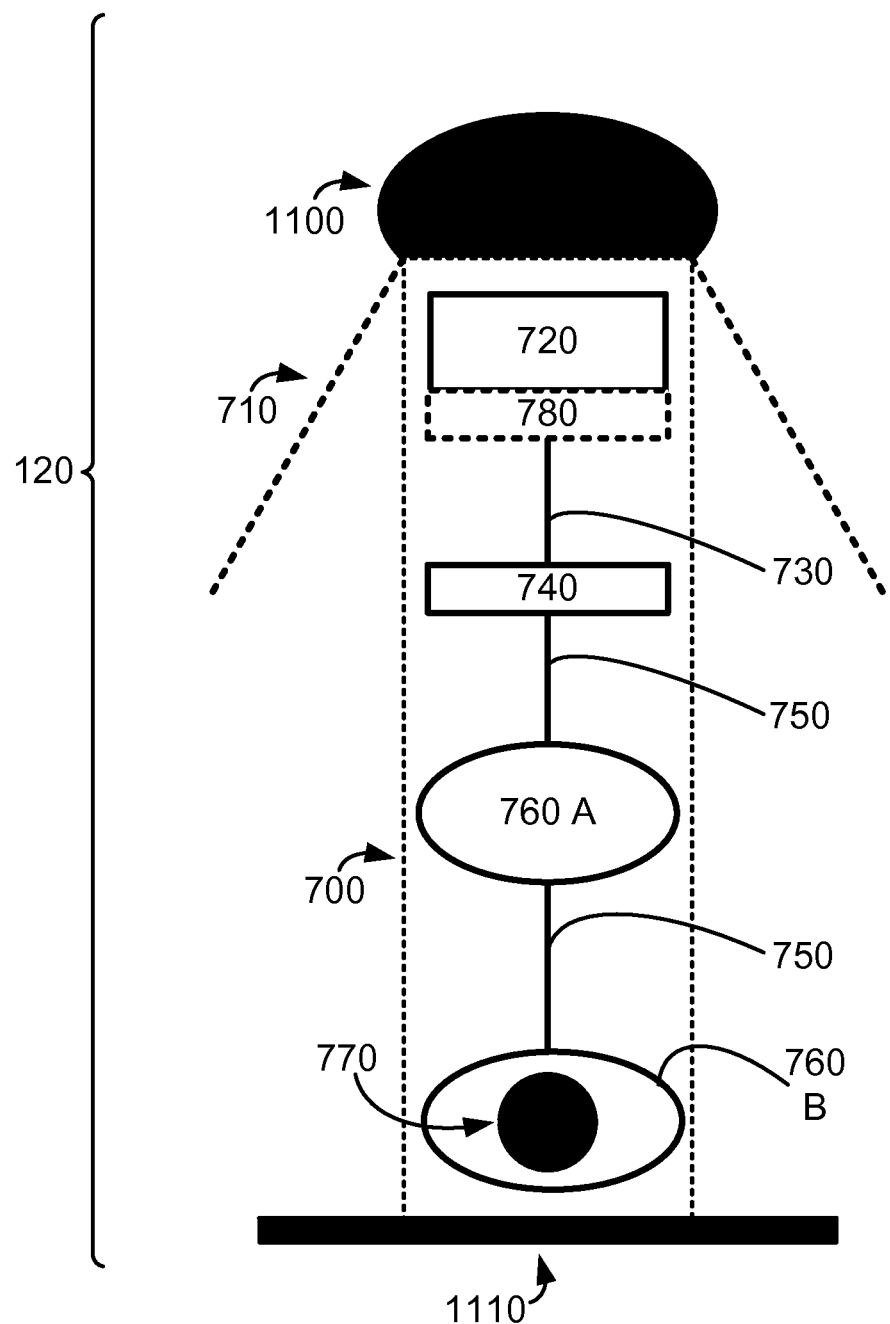
FIG. 12 is a schematic of an appurtenance to a wound dressing.

FIG. 12 illustrates an appurtenance 120 to a wound dressing in a substantially cross-section view to illustrate internal features of the appurtenance 120. The appurtenance 120 illustrated in FIG. 12 includes an enclosure 700 that is a substantially cylindrical structure that is hollow, with an internal region. The appurtenance 120 includes a positioning element 1100 affixed to an end of the enclosure 700. The appurtenance 120 includes a flange 710 affixed to an exterior surface of the enclosure at a first end, which is also adjacent to the positioning element 1100. The enclosure 700 includes an aperture 770. The appurtenance 120 includes an end cap 1110 affixed to a second end of the appurtenance 120, which is distal to the positioning element 1100.

The embodiment of an appurtenance 120 shown in FIG. 12 includes a first sensor unit 760 A internal to the enclosure 700. A first sensor unit can include, for example, a resonance sensor, a temperature sensor, or a pressure sensor. The appurtenance 120 includes a second sensor unit 760 B positioned adjacent to the aperture 700. For example, some embodiments include a sensor unit positioned to detect characteristics of the wound fluid within a wound dressing. The first sensor unit 760 A and the second sensor unit 760 B are connected to each other and to a processor 740 with a wire connector 750. The processor 740 is connected to a transmission unit 720 with a wire connector 730. A battery unit 780 can also be attached to the transmission unit, depending on the embodiment.

Figure 13:
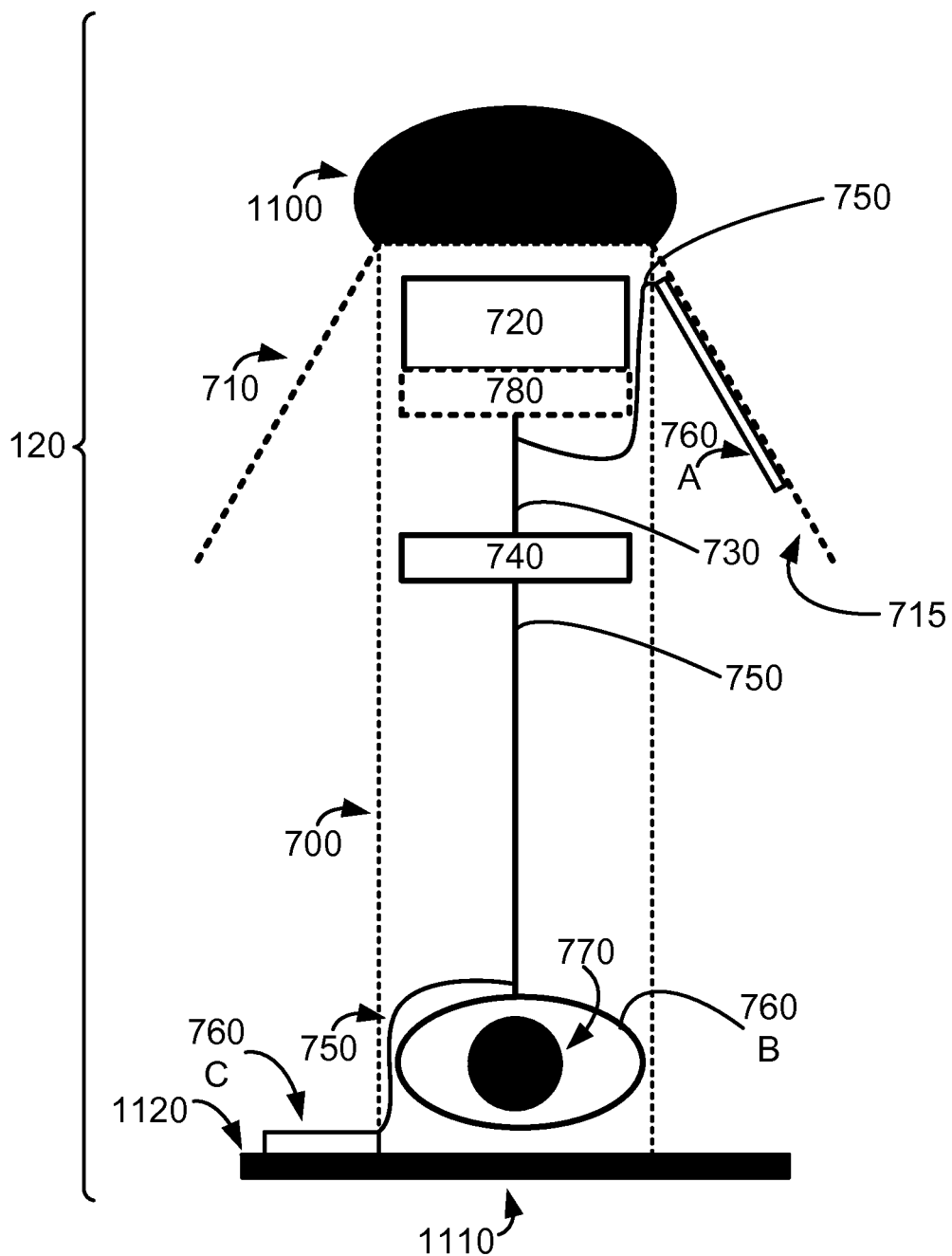
FIG. 13 is a schematic of an appurtenance to a wound dressing.

FIG. 13 illustrates an appurtenance 120 to a wound dressing in a substantially cross-section view to illustrate internal features of the appurtenance 120. The appurtenance 120 illustrated in FIG. 13 includes an enclosure 700 that is a substantially cylindrical structure that is hollow, with an internal region. The appurtenance 120 includes a positioning element 1100 affixed to an end of the enclosure 700. The appurtenance 120 includes a flange 710 affixed to an exterior surface of the enclosure at a first end, which is also adjacent to the positioning element 1100. The enclosure 700 includes an aperture 770. The appurtenance 120 includes an end cap 1110 affixed to a second end of the appurtenance 120, which is distal to the positioning element 1100.

The embodiment of an appurtenance 120 shown in FIG. 13 includes a first sensor unit 760 A affixed to a surface 715 of the flange 710 positioned to contact a surface of a wound dressing when the appurtenance 120 is in use with a wound dressing. For example, in some embodiments a first sensor unit affixed to the flange can include one or more of: a temperature sensor, or a pressure sensor. The first sensor unit 760 A is connected to a processor and a transmission unit 720 with wire connectors 750, 730. The appurtenance 120 includes a second sensor unit 760 B positioned within the enclosure at a location adjacent to the aperture 770. For example, some embodiments include a sensor unit positioned to detect characteristics of the wound fluid within a wound dressing. The second sensor unit 760 B is connected to the processor 740 with a wire connector 750. The embodiment illustrated in FIG. 13 includes a third sensor unit 760 C affixed to the end cap 1110 on the surface adjacent to an expected position of the wound dressing. For example, in some embodiments a sensor unit affixed to the end cap can include one or more of: a pressure sensor, a sensor unit configured to detect components of wound fluid, and/or a temperature sensor. Some embodiments include a battery 780 attached to the transmission unit 720 and/or the processor 740, for example with a wire connector 730.

Figure 14A:
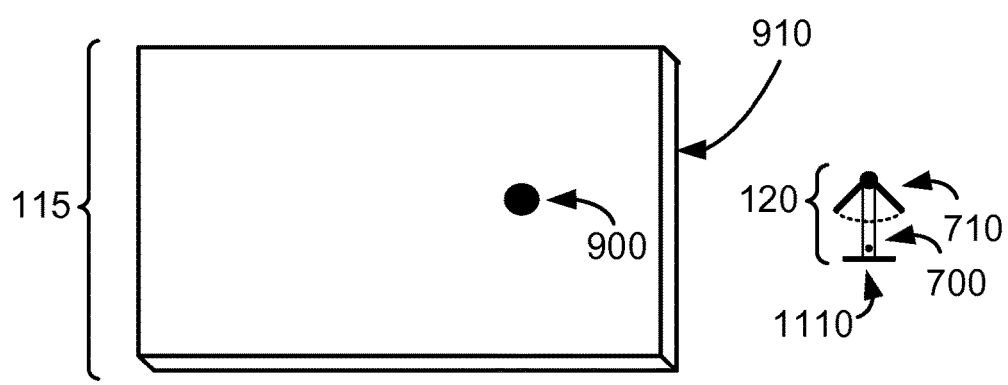
FIG. 14A is a schematic of an appurtenance and a wound dressing.

FIG. 14A illustrates aspects of an appurtenance 120 and a wound dressing 115. The appurtenance is configured for use with a subset of wound dressings of a predetermined approximate thickness and appropriately sized and shaped aperture. The appurtenance 120 includes an enclosure 700, with a flange 710 affixed to a first end of the enclosure 700 and an end cap 1110 affixed to the second end of the enclosure 700. The appurtenance 120 is fabricated with a size and shape for use with a substantially planar wound dressing 115 with a thickness 910 similar to the height of the enclosure of the appurtenance 120. The wound dressing 115 includes an aperture 900 with an interior surface of a size and shape to mate with the exterior surface of the enclosure of the appurtenance 120. The aperture 900 in the wound dressing can be positioned at a location of particular interest in wound monitoring, for example adjacent to a wound cavity. The aperture 900 in the wound dressing can be positioned at a location expected to result in minimal discomfort to the patient, for example at a position distal to a wound surface.

Figure 14B:
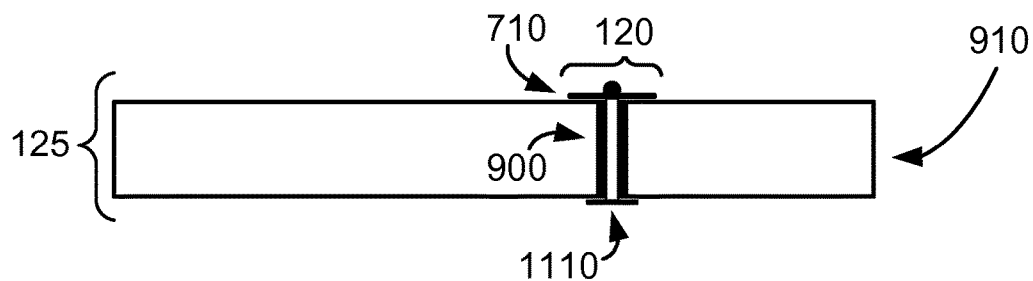
FIG. 14B is a schematic of an appurtenance attached to a wound dressing.

FIG. 14B illustrates an appurtenance and wound dressing similar to those shown in FIG. 14A, positioned as an appurtenance-wound dressing combination unit 125. The appurtenance 120 is positioned within the aperture 900 in the wound dressing, and has a long axis that is a similar dimension to the thickness 910 of the wound dressing. The flange 710 has flexed outward from the exterior surface of the enclosure 700, so that the flange 710 is positioned as substantially parallel to a surface of the wound dressing then the appurtenance is in place for use. The enclosure of the appurtenance 120 traverses the aperture 900 in the wound dressing. At the end of the appurtenance 120 distal to the flange 710, the end cap 1110 is positioned adjacent to the surface of the wound dressing. In some embodiments, an end cap is of a size and shape to be positioned adjacent to the aperture on an exterior surface of the wound dressing. In some embodiments, an end cap is of a size and shape to be positioned within the aperture at a location adjacent to the end of the aperture.

Some embodiments include an appurtenance to a wound dressing, including: a substrate with a surface of a size and shape to mate with a surface of a wound dressing; a resonance sensor affixed to the substrate; and an attachment unit of a size and shape to affix the substrate to the wound dressing with the surface in direct contact with the surface of the wound dressing. In some embodiments, a resonance sensor includes: a passive RFID unit including a cavity resonator. Some embodiments include wherein the resonance sensor includes a passive RFID unit including a cavity resonator of a size and shape to have dampened resonance within the cavity resonator when the wound dressing is substantially saturated with fluid, and further including a passive RFID including a unique identifier and a self-compensating antenna calibrated for use with the wound dressing. Since fluid from a wound, including blood and pus, is a dielectric material, a wound dressing full of fluid from a wound will have different dielectric properties when it is dry than it does when it is saturated with wound fluid. Some embodiments include at least a first RFID unit that includes a mechanism for compensating for resonance changes in connection with a dry wound dressing and also when the wound dressing is substantially saturated, and a second RFID unit with structure that will be functional in association with the dry wound dressing and dampened in connection when the wound dressing is substantially saturated with fluid from the wound. See, for example, U.S. Pat. No. 7,055,754 to Forster, titled "Self-Compensating Antennas for Substrates Having Differing Dielectric Constant Values," which is incorporated herein by reference.

Some embodiments include a wound dressing monitoring system, including: a wound dressing including at least one aperture; and an appurtenance, including an enclosure including at least one external surface of a size and shape to mate with an internal surface of the aperture in the wound dressing, one or more sensor units affixed to the enclosure, a processor operably attached to the one or more sensor units, and at least one transmission unit operably attached to the processor, the transmission unit including circuitry configured to transmit information associated with the one or more sensor units. Some embodiments include a wound dressing monitoring kit, including: a wound dressing of a size and shape, and an appurtenance of a size and shape to conform with the size and shape of the wound dressing. Some wound dressings for use with an appurtenance include at least one aperture of a size, shape and position to mate with the surface of an appurtenance.

Figure 15A:
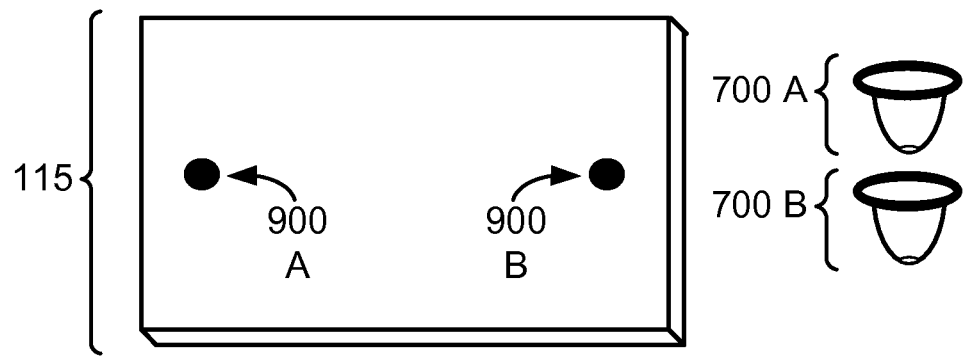
FIG. 15A is a schematic of two appurtenance enclosures and a wound dressing.

FIG. 15A illustrates modular aspects of an appurtenance to a wound dressing and a wound dressing for use with the appurtenance. The embodiment shown in FIG. 15A includes a wound dressing 115 including a first aperture 900 A and a second aperture 900 B. Some embodiments include apertures positioned at opposing ends of the wound dressing. Some embodiments include apertures positioned in a regular pattern on the wound dressing, for example apertures positioned along an axis, and/or apertures positioned at regular intervals along the length of the wound dressing. FIG. 15A depicts two enclosures 700 A and 700 B of a size and shape for use with the wound dressing 115 and its apertures 900 A, 900 B. The enclosures 700 A and 700 B are of a size and shape to mate with the interior surfaces of the apertures, including an appropriate height relative to the thickness of the wound dressing.

Figure 15B:
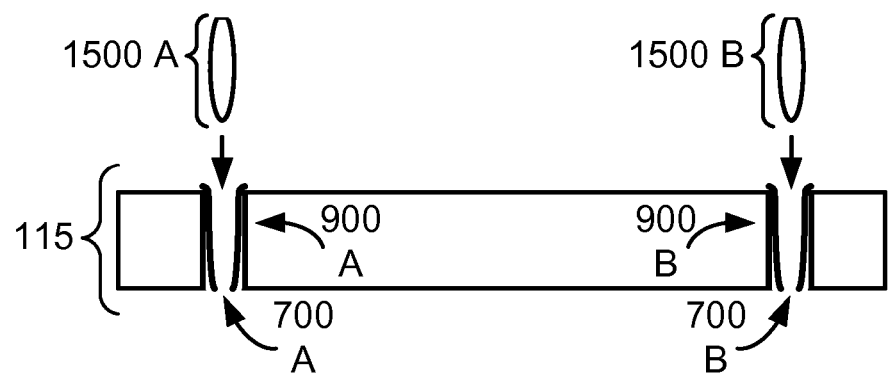
FIG. 15B is a schematic of two appurtenance enclosures attached to a wound dressing as well as two sensor inserts.

FIG. 15B illustrates a wound dressing 115 including two apertures, 900 A 900 B. The wound dressing 115 is shown at a side view in substantial cross-section for purposes of illustration. The two apertures 900 A, 900 B each have an enclosure 700 A, 700 B positioned within the aperture. The enclosures 700 A, 700 B are each positioned with a top adjacent to a first planar surface of the wound dressing 115 and a bottom adjacent to a second planar surface of the wound dressing 115, wherein the first planar surface of the wound dressing 115 and the second planar surface of the wound dressing 115 are positioned on opposing faces of the wound dressing 115. Two modular inserts 1500 A, 1500 B are positioned adjacent to the apertures 900 A, 900 B. The modular inserts include components of the appurtenance. For example, in some embodiments a modular insert includes one or more of: one or more sensor units; a processor; a transmission unit; and a battery. A modular insert can also include a fluid transport film, for example positioned adjacent to a sensor unit and oriented to direct fluid toward the sensor unit. A modular insert can also include a fluid control film, for example surrounding a battery and/or a transmission unit in order to insulate those components from fluid within the enclosure. In some embodiments, a wound dressing is fabricated and shipped to medical consumers with one or more apertures including affixed enclosures, and modular units are inserted at the time of use by a user of the wound dressing. Modular units can be included in the packaging of the wound dressing. In some embodiments, modular units are replaceable.

Figure 15C:
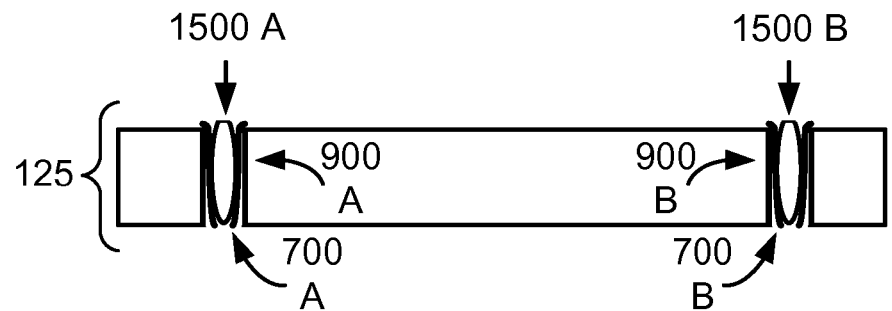
FIG. 15C is a schematic of two appurtenance enclosures attached to a wound dressing with sensor inserts within each of the appurtenance enclosures.

FIG. 15C illustrates a wound dressing 115 at a side view in substantial cross-section for purposes of illustration, similar to the view of FIG. 15B. The two apertures 900 A, 900 B each have an enclosure 700 A, 700 B positioned within the aperture, and a modular insert 1500 A, 1500 B positioned within each of the enclosures 700 A, 700 B. The modular inserts 1500 A, 1500 B include an external surface of a size and shape to mate with the interior surface of an enclosure 700 A, 700 B. Some embodiments include a plurality of modular units with the same components. For example, some embodiments include modular units with the same type of sensor units, and/or the same type of transmission units. Some embodiments include a plurality of modular units with different components. For example, some embodiments include modular units with different types of sensor units, and/or different types of transmission units.

Some embodiments include a wound dressing monitoring system. For example, a wound dressing monitoring system can be packaged for the convenience of the user to include a wound dressing, including at least one aperture, and an appurtenance of a size and shape for use within the aperture of the wound dressing. In some embodiments, a wound dressing monitoring system is packaged as a kit. In some embodiments, a wound dressing monitoring system includes: a wound dressing including at least one aperture; and an appurtenance, including an enclosure including at least one external surface of a size and shape to mate with an internal surface of the aperture in the wound dressing, one or more sensor units affixed to the enclosure, a processor operably attached to the one or more sensor units, and at least one transmission unit operably attached to the processor. In some embodiments, a wound dressing monitoring system includes: a wound dressing including an aperture; and an appurtenance, including an enclosure including at least one external surface of a size and shape to mate with an internal surface of the aperture in the wound dressing and affixed within the aperture, and a modular unit including one or more sensor units, a processor operably attached to the one or more sensor units, and at least one transmission unit operably attached to the processor. In some embodiments a wound dressing monitoring system includes a wrapper sealed to protect the cleanliness and/or sterility of the wound monitoring system.

EXAMPLES

Example 1: An Appurtenance Including a Resonance Sensor

An appurtenance to a wound dressing is fabricated to include a resonance sensor positioned for detection of substantial saturation of a wound dressing with wound fluid. The appurtenance includes a substrate with a surface of a size and shape to mate with a substantially planar surface of a wound dressing. The substrate is fabricated from a polypropylene sheet of approximately 0.5 mm in thickness. The appurtenance includes an attachment unit of a size and shape to affix the substrate to the wound dressing, with the surface of the substrate in direct contact with the surface of the wound dressing. The attachment unit of the appurtenance includes a projection of a size and shape to be affixed to an aperture of a corresponding size and shape in the wound dressing. The projection of the attachment unit is positioned at substantially right angles to the surface of the substrate of a size and shape to mate with a surface of a wound dressing. The attachment unit is fabricated from a firm PET plastic. The attachment unit includes a ring of a size and shape to mate with the end of the projection and clamp on, thereby securing the projection within the aperture in the wound dressing.

A resonance sensor is affixed to the substrate. The resonance sensor includes a passive RFID unit with a cavity resonator of a size and shape to come into contact at a surface with the wound dressing when the appurtenance is in place. The cavity resonator is of a sufficient size for adjacent fluid in the wound dressing to dampen the cavity resonance during use. For a wound dressing that includes a gauze sponge that is a four inch square (i.e. a "4×4") on its largest surface and 12-ply thickness, a passive RFID unit is selected that includes a cavity resonator that is one inch square.

Prior to use, a 4×4, 12-ply gauze sponge wound dressing is selected with a precut aperture of a size and shape to mate with the exterior surface of the projection. The projection is pushed through the aperture and the appurtenance secured in place with the attachment of the ring. The resonance sensor, including the passive RFID with the cavity resonator, is positioned against the surface of the wound dressing away from the surface intended for use with a wound.

Example 2: Test Use of an Appurtenance Including a Resonance Sensor

A test device for an appurtenance including a resonance sensor was constructed including a plastic block with a substantially planar top surface approximately 4.5 inches square. A substantially horizontal channel was cut in the side of the block, and connected to an external section of tubing. Multiple vertical channels were cut into the block from the top surface to the substantially horizontal channel internal to the block. During use, fluid from a syringe attached to the external tubing was pushed into the block where it flowed through the internal channels and out of the vertical channels connecting to the top surface of the block. The fluid flow was used to mimic fluid of a wound under a wound dressing for testing purposes.

A metal frame was constructed of aluminum. The metal frame was fabricated to be a size and shape to mate with the external edge of the top surface of the block. The metal frame was approximately one half inch wide and of sufficient thickness and mass to hold the edges of a wound dressing in position against the top surface of the block during testing, while leaving the center of the wound dressing uncovered.

A 4×4, 12-ply gauze sponge wound dressing with an attached appurtenance including a resonance sensor as described in Example 1 was selected for testing. The wound dressing-appurtenance combination unit was positioned on the top of the block. The metal frame was placed over the wound dressing edges, securing the lower surface of the wound dressing against the top surface of the block.

A handheld RFID reader was used to scan the dry wound dressing-appurtenance combination unit on the test block from a distance of approximately 6 inches. The handheld reader was able to detect the passive RFID within the resonance sensor affixed to the dry wound dressing. Software within the reader was configured to indicate the detection on a screen with the text "dressing OK." Fluid was then pushed into the block from an attached syringe, and the wound dressing became visibly wet within 30 seconds. After the wound dressing was visibly wet, the handheld reader was used to scan the wet wound dressing-appurtenance combination unit on the test block from a distance of approximately 6 inches. The handheld reader was not able to detect the passive RFID within the resonance sensor affixed to the wet wound dressing. Software within the reader was configured to indicate the lack of detection on a screen with the text "check dressing."

The herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some implementations described herein, logic and similar implementations may include computer programs or other control structures. Electronic circuitry, for example, may have one or more paths of electrical current constructed and arranged to implement various functions as described herein. In some implementations, one or more media may be configured to bear a device-detectable implementation when such media hold or transmit device detectable instructions operable to perform as described herein. In some variants, for example, implementations may include an update or modification of existing software (e.g., a high-level computer program serving as a hardware specification) or firmware, or of gate arrays or programmable hardware, such as by performing a reception of or a transmission of one or more instructions in relation to one or more operations described herein. Alternatively or additionally, in some variants, an implementation may include special-purpose hardware, software (e.g., a high-level computer program serving as a hardware specification), firmware components, and/or general-purpose components executing or otherwise invoking special-purpose components. Specifications or other implementations may be transmitted by one or more instances of tangible transmission media as described herein, optionally by packet transmission or otherwise by passing through distributed media at various times.

Alternatively or additionally, implementations may include executing a special-purpose instruction sequence or invoking circuitry for enabling, triggering, coordinating, requesting, or otherwise causing one or more occurrences of virtually any functional operation described herein. In some variants, operational or other logical descriptions herein may be expressed as source code and compiled or otherwise invoked as an executable instruction sequence. In some contexts, for example, implementations may be provided, in whole or in part, by source code, such as C++, or other code sequences. In other implementations, source or other code implementation, using commercially available and/or techniques in the art, may be compiled//implemented/translated/converted into a high-level descriptor language (e.g., initially implementing described technologies in C or C++ programming language and thereafter converting the programming language implementation into a logic-synthesizable language implementation, a hardware description language implementation, a hardware design simulation implementation, and/or other such similar mode(s) of expression). For example, some or all of a logical expression (e.g., computer programming language implementation) may be manifested as a Verilog-type hardware description (e.g., via Hardware Description Language (HDL) and/or Very High Speed Integrated Circuit Hardware Descriptor Language (VHDL)) or other circuitry model which may then be used to create a physical implementation having hardware (e.g., an Application Specific Integrated Circuit). Those skilled in the art will recognize how to obtain, configure, and optimize suitable transmission or computational elements, material supplies, actuators, or other structures in light of these teachings.

In an embodiment, several portions of the subject matter described herein may be implemented via Application Specific Integrated Circuits (ASICs), Field Programmable Gate Arrays (FPGAs), digital signal processors (DSPs), or other integrated formats. However, some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software (e.g., a high-level computer program serving as a hardware specification) and or firmware would be well within the skill of one of skill in the art in light of this disclosure.

In a general sense, the various embodiments described herein can be implemented, individually and/or collectively, by various types of electro-mechanical systems having a wide range of electrical components such as hardware, software (e.g., a high-level computer program serving as a hardware specification), firmware, and/or virtually any combination thereof, and a wide range of components that may impart mechanical force or motion such as rigid bodies, spring or torsional bodies, hydraulics, electro-magnetically actuated devices, and/or virtually any combination thereof. Consequently, as used herein "electro-mechanical system" includes, but is not limited to, electrical circuitry operably coupled with a transducer (e.g., an actuator, a motor, a piezoelectric crystal, a Micro Electro Mechanical System (MEMS), etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, communications switch, optical-electrical equipment, etc.), and/or any non-electrical analog thereto, such as optical or other analogs (e.g., graphene based circuitry). Examples of electro-mechanical systems include but are not limited to a variety of consumer electronics systems, medical devices, as well as other systems such as motorized transport systems, factory automation systems, security systems, and/or communication/computing systems. "Electro-mechanical," as used herein, is not necessarily limited to a system that has both electrical and mechanical actuation except as context may dictate otherwise.

In a general sense, the various aspects described herein which can be implemented, individually and/or collectively, by a wide range of hardware, software (e.g., a high-level computer program serving as a hardware specification), firmware, and/or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), and/or electrical circuitry forming a communications device (e.g., a modem, communications switch, optical-electrical equipment, etc.). The subject matter described herein may be implemented in an analog or digital fashion or some combination thereof.

All of the above U.S. patents, U.S. patent application publications, U.S. patent applications, foreign patents, foreign patent applications and non-patent publications referred to in this specification and/or listed in any Application Data Sheet, are incorporated herein by reference, to the extent not inconsistent herewith.

While various aspects and embodiments have been disclosed herein, other aspects and embodiments will be apparent. The various aspects and embodiments disclosed herein are for purposes of illustration and are not intended to be limiting, with the true scope and spirit being indicated by the following claims.

What is claimed is:

1. An appurtenance to a wound dressing, comprising:
a substrate with at least one surface of a size and shape to mate with a surface of the wound dressing;
a plurality of projections attached to the substrate and positioned to secure the substrate to the wound dressing, the plurality of projections extending outward in substantially the same plane as the surface of the substrate, wherein a first set of the plurality of projections is attached to the substrate and extends in a first direction from the substrate, and a second set of the plurality of projections is attached to the substrate and extends in a second direction from the substrate, the second direction different than the first direction;
one or more sensor units attached to the substrate, the one or more sensor units configured to sense a condition of the wound dressing; and
a transmission unit attached to the substrate and operably coupled to the one or more sensor units, the transmission unit including circuitry configured to transmit information associated with the sensed condition of the wound dressing sensed by the one or more sensor units.

2. The appurtenance of claim 1, wherein the substrate comprises:
a substantially planar structure.

3. The appurtenance of claim 1, wherein the substrate comprises:
a flexible structure.

4. The appurtenance of claim 1, wherein the one or more sensor units comprise:
a chemical sensor.

5. The appurtenance of claim 1, wherein the one or more sensor units comprise:
a resonance sensor.

6. The appurtenance of claim 1, wherein the one or more sensor units comprise:
a plurality of sensors within each sensor unit.

7. The appurtenance of claim 1, further comprising:
a desiccant material in fluid communication with the wound dressing.

8. The appurtenance of claim 1, wherein:
the at least one of the plurality of projections defines a first aperture at a distal end of the at least one projection, and defines a channel in fluid communication from the first aperture to a second aperture defined at a proximate end by the at least one of the plurality of projections, the second aperture positioned adjacent to the substrate; and
an enclosed tubular structure attached to the substrate, the enclosed tubular structure affixed to the second aperture at a first end, the tubular structure affixed to the one or more sensor units at a second end.

9. The appurtenance of claim 8, further comprising:
a gas-sealed chamber attached to the enclosed tubular structure, the gas-sealed chamber including an internal gas pressure below atmospheric pressure; and
a breakable seal between the gas-sealed chamber and the enclosed tubular structure.

10. The appurtenance of claim 1, further comprising:
at least one flexible divider internal to the substrate;
wherein the one or more sensors includes a first sensor unit and a second sensor unit; and
wherein the at least one flexible divider is positioned between the first sensor unit and the second sensor unit.

11. The appurtenance of claim 1, further comprising:
a fluid transport film affixed to the substrate.

12. The appurtenance of claim 1, further comprising:
a fluid control film affixed to the substrate.

13. An appurtenance to a wound dressing, comprising:
a substrate including a first wall and a second, opposing wall, the substrate including at least one divider positioned inside the substrate and extending between the first wall and the second wall and positioned between a first sensor unit and a second sensor unit;
a plurality of projections attached to the substrate and positioned to secure the substrate to the wound dressing, the plurality of projections extending outward in substantially the same plane as the surface of the substrate;
one or more sensor units attached to the substrate, the one or more sensor units configured to sense a condition of the wound dressing, wherein the one or more sensor units includes the first sensor unit and the second sensor unit; and
a transmission unit attached to the substrate and operably coupled to the one or more sensor units, the transmission unit including circuitry configured to transmit information associated with the sensed condition of the wound dressing sensed by the one or more sensor units.

14. The appurtenance of claim 13, wherein at least one of the first unit or the second sensor unit comprise a plurality of sensors within each sensor unit.

15. The appurtenance of claim 13, wherein the substrate comprises a substantially planar structure.

16. The appurtenance of claim 13, wherein at least one of the substrate or the at least one divider is flexible.

17. The appurtenance of claim 13, further comprising a desiccant material in fluid communication with the wound dressing.

18. The appurtenance of claim 13, wherein the substrate comprises:
a first terminal end, with a first set of the plurality of projections attached to the first terminal end of the substrate; and
a second terminal end, with a second set of the plurality of projections attached to the second terminal end of the substrate.

* * * * *